United States Patent
Wakamiya et al.

(10) Patent No.: US 8,040,757 B2
(45) Date of Patent: Oct. 18, 2011

(54) SAMPLE ANALYZING APPARATUS

(75) Inventors: Yuji Wakamiya, Hyogo (JP); Tomohiro Okuzaki, Hyogo (JP); Hisato Takehara, Hyogo (JP)

(73) Assignee: Sysmex Corporation, Kobe (JP)

( * ) Notice: Subject to any disclaimer, the term of this patent is extended or adjusted under 35 U.S.C. 154(b) by 512 days.

(21) Appl. No.: 12/150,142

(22) Filed: Apr. 25, 2008

(65) Prior Publication Data

US 2008/0279048 A1 Nov. 13, 2008

(30) Foreign Application Priority Data

Apr. 27, 2007 (JP) ................................. 2007-119770
May 8, 2007 (JP) ................................. 2007-123999

(51) Int. Cl.
*G04B 47/00* (2006.01)
*G04C 17/00* (2006.01)
*G01N 21/00* (2006.01)

(52) U.S. Cl. ............................... 368/10; 368/29; 422/67

(58) Field of Classification Search .................... 368/10, 368/28, 29; 422/67; 702/22
See application file for complete search history.

(56) References Cited

U.S. PATENT DOCUMENTS

| | | | | |
|---|---|---|---|---|
| 4,939,095 A | * | 7/1990 | Yokotani | 436/47 |
| 5,314,825 A | * | 5/1994 | Weyrauch et al. | 436/43 |
| 5,473,551 A | * | 12/1995 | Sato et al. | 702/19 |
| 5,920,727 A | * | 7/1999 | Kikinis et al. | 713/323 |
| 6,049,776 A | * | 4/2000 | Donnelly et al. | 705/8 |
| 6,080,364 A | * | 6/2000 | Mimura et al. | 422/67 |
| 6,544,476 B1 | * | 4/2003 | Mimura et al. | 422/67 |
| 6,611,275 B1 | * | 8/2003 | Zey et al. | 715/752 |
| 6,925,574 B2 | * | 8/2005 | Satoh | 713/323 |
| 7,185,288 B2 | * | 2/2007 | McKeever | 715/792 |
| 2005/0175506 A1 | * | 8/2005 | Matsubara et al. | 422/68.1 |
| 2007/0212261 A1 | * | 9/2007 | Tanaka et al. | 422/67 |
| 2008/0050280 A1 | * | 2/2008 | Fujita | 422/67 |

FOREIGN PATENT DOCUMENTS

JP 09-211003 8/1997

* cited by examiner

*Primary Examiner* — Vit Miska
(74) *Attorney, Agent, or Firm* — Brinks Hofer Gilson & Lione

(57) ABSTRACT

A sample analyzing apparatus is provided with a memory for storing a schedule of maintenance, a display, and a controller for displaying on the display a screen of calendar format, wherein the screen includes a date display area for displaying a date and a maintenance item display area for displaying a maintenance item scheduled on the date.

17 Claims, 16 Drawing Sheets

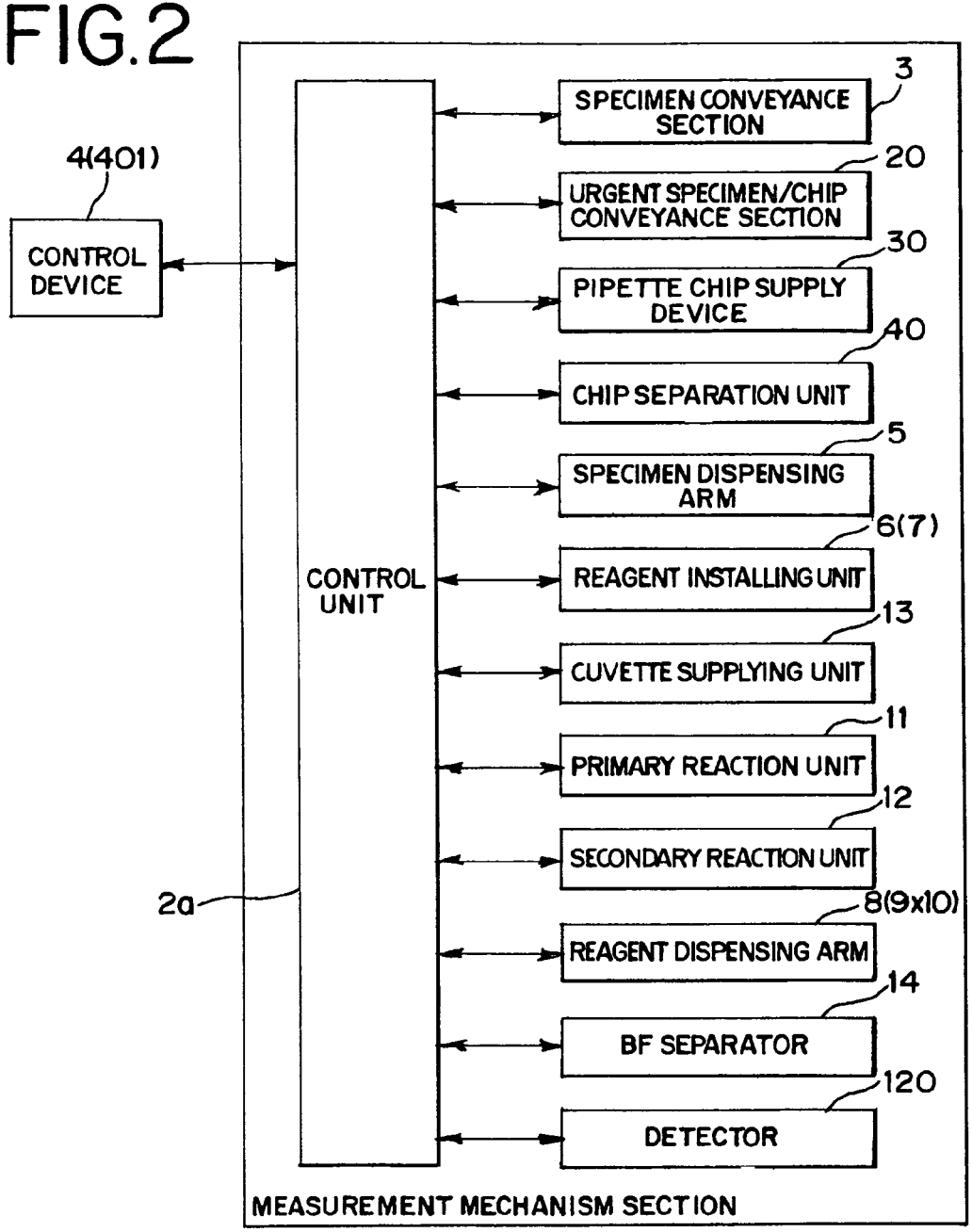
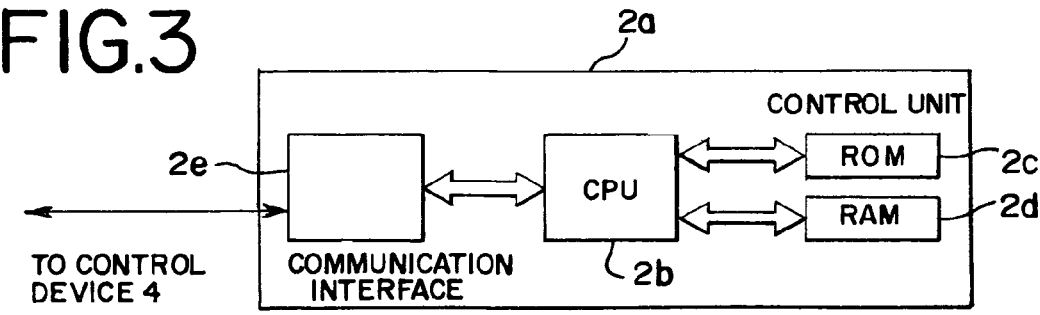

SAMPLE ANALYZING APPARATUS

CROSS REFERENCE TO RELATED APPLICATION

This application claims the benefit of priority from Japanese Patent Application No. 2007-119770 filed on Apr. 27, 2007 and Japanese Patent Application No. 2007-123999 filed on May 8, 2007, the entire disclosure of which is incorporated herein by reference.

FIELD OF THE INVENTION

The present invention relates to a sample analyzing apparatus equipped with a measuring unit for measuring a specimen that enables the user to easily acquire the maintenance schedule of the measuring unit.

BACKGROUND

Specimen analyzers such as colorimetric analyzer, fluorescence analyzer, immune analyzer, blood coagulation analyzer, and blood analyzer are known as a specimen measuring apparatus for analyzing a measurement sample prepared from a specimen and a reagent.

In this type of specimen analyzer, a measuring unit for preparing the measurement sample by processing a specimen using various reagents, and optically or electrically measuring the obtained measurement sample is arranged.

The process from preparation of the measurement sample to the measurement of the measurement sample in the measuring unit always needs to be smoothly performed in order to maintain the analyzing accuracy of the specimen analyzer. Thus, maintenance of the measuring unit of the specimen analyzer needs to be performed according to a predetermined schedule for the necessary maintenance items. The maintenance items of the immune analyzer include, for example, "pipette washing" of the pipette for dispensing the reagent; "discard cuvette" of discarding the used cuvette (sample tube) accommodated in the discarding container, and emptying the container; "waste process" of the used washing liquid and the like; order task of consumable goods (pipette chip used in dispensing reagent and specimen, cuvette for accommodating and optically detecting the dispensed reagent) used in the specimen analyzer, and the like.

Japanese Laid-Open Patent Publication No. 9-211003 discloses an automatic analyzer in which when the maintenance item is executed, the executed date is stored in the storage device. In the automatic analyzer, the user can newly register the maintenance item other than the maintenance items registered in advance. The automatic analyzer has an alarm function of notifying a timing of performing maintenance on the registered maintenance items to the user.

In the analyzer disclosed in Japanese Laid-Open Patent Publication No. 9-211003, the record of the maintenance is displayed on the maintenance screen, and the maintenance item name, where warning alarm is issued, and the date and time thereof are displayed in time-series from the oldest, for example, as shown in FIG. 9 of the publication.

On the screen, twelve maintenance records are displayed from the oldest record, and the maintenance record of a new date and time can be displayed by scrolling the screen.

However, in the analyzer disclosed in Japanese Laid-Open Patent Publication No. 9-211003, the record of maintenance can be checked, but the schedule of maintenance cannot be checked. Therefore, if the user wants to check the schedule of a maintenance task, in particular, wants to check the schedule of maintenance task of three days, one week, two weeks etc. later, the schedule of the maintenance task cannot be easily acquired.

BRIEF SUMMARY OF THE INVENTION

In view of the above, it is an object of the present invention to provide a specimen measuring apparatus enabling the user to easily acquire the schedule of the maintenance task of the specimen analyzer.

A sample analyzing apparatus embodying features of the present invention includes a memory for storing a schedule of maintenance; a display; and a controller for displaying on the display a screen of calendar format, wherein the screen includes a date display area for displaying a date and a maintenance item display area for displaying a maintenance item scheduled on the date.

A maintenance schedule displaying method embodying features of the present invention includes steps of providing a screen of calendar format, which includes a date display area for displaying a date and a maintenance item display area for displaying a maintenance item scheduled on the date; and displaying the screen on a display of the sample analyzing apparatus.

BRIEF DESCRIPTION OF THE DRAWINGS

FIG. 2 is a block diagram showing a configuration of a measuring apparatus of the immune analyzer shown in FIG. 1;

FIG. 3 is a block diagram showing a configuration of a control unit of the measuring apparatus shown in FIG. 2;

DETAILED DESCRIPTION OF THE PREFERRED EMBODIMENTS

The preferred embodiments of the present invention will be described hereinafter with reference to the drawings.

Figure 1:
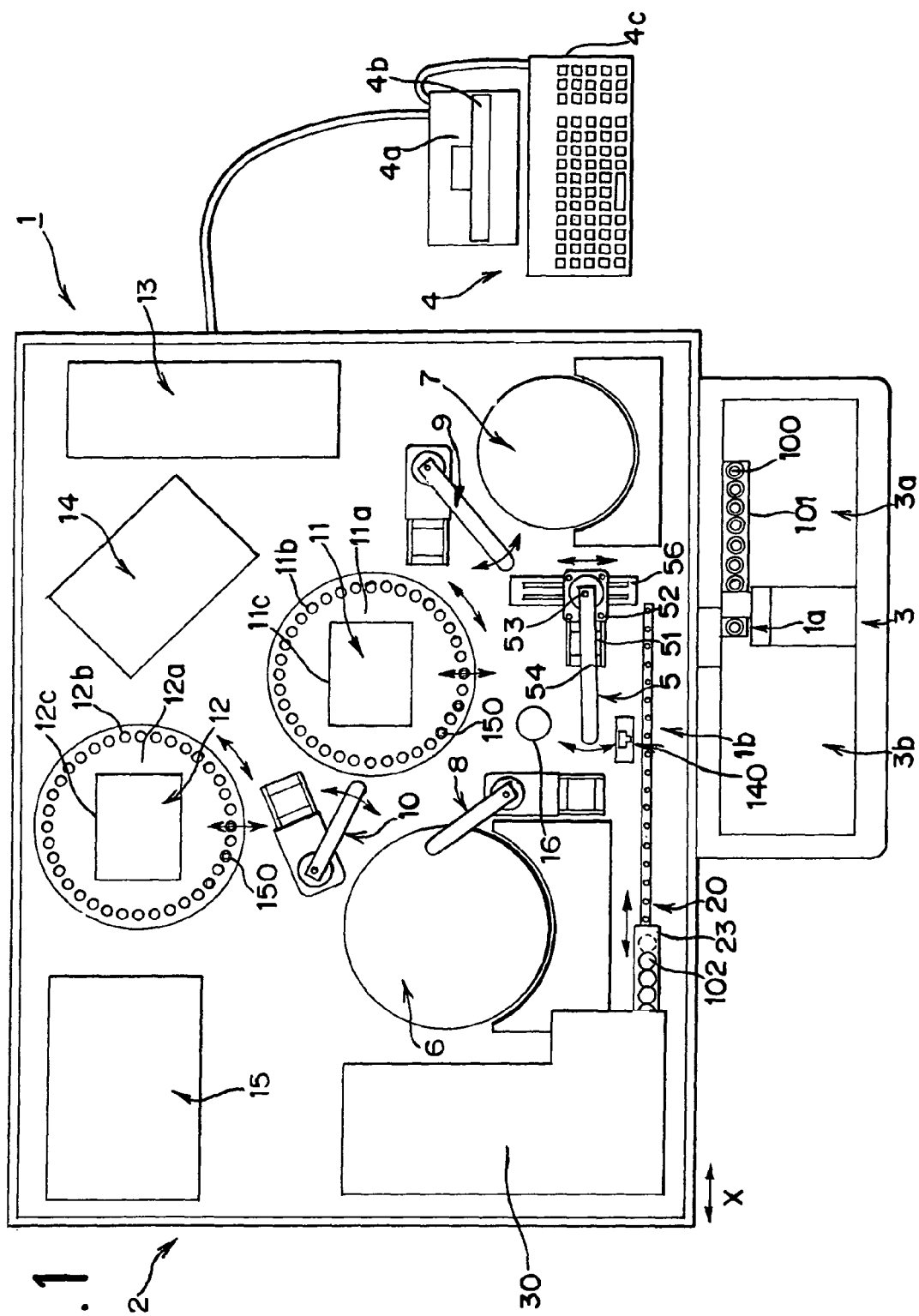
FIG. 1 is a plan view showing an overall configuration of an immune analyzer according to one embodiment of the present invention.
Figure 4:
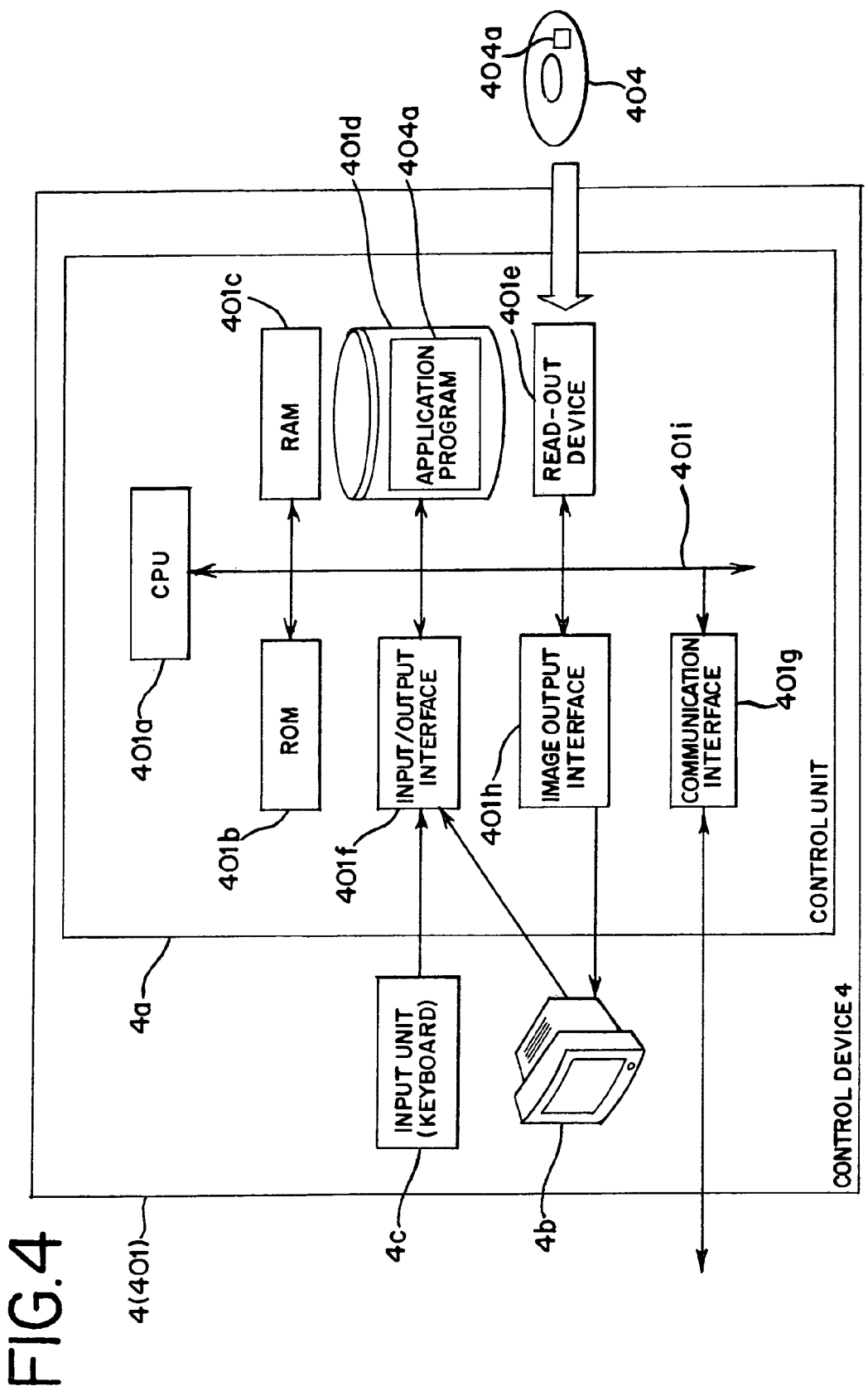
FIG. 4 is a block diagram showing a configuration of a control device of the immune analyzer shown in FIG. 1.

FIG. 1 is a plan view showing an overall configuration of an immune analyzer according to one embodiment of the present invention. FIG. 2 is a block diagram showing a configuration of a measuring apparatus of the immune analyzer shown in FIG. 1, and FIG. 3 is a block diagram showing a configuration of a control unit of the measuring apparatus. FIG. 4 is a block diagram showing a configuration of a control device of the immune analyzer shown in FIG. 1. First, the overall configuration of the immune analyzer according to one embodiment of the present invention will be described with reference to FIGS. 1 to 4.

The immune analyzer 1 according to one embodiment of the present invention is an apparatus for carrying out examinations on various items such as hepatitis B, hepatitis C, tumor marker, and thyroid hormone using specimen such as blood. In the immune analyzer 1, magnetic particles (R2 reagent) are bonded to a trapped antibody (R1 reagent) bonded to an antigen contained in a specimen such as blood, which is the measurement object, and thereafter, the bound antigen, trapped antibody, and magnetic particles are attracted to a magnet (not shown) of a BF (Bound Free) separator 14 (see FIGS. 1 and 2) to remove the R1 reagent containing non-reacting (free) trapped body. A labeled antibody (R3 reagent) is bonded to the antigen bound with magnetic particles, and thereafter, the bound magnetic particles, antigen, and labeled antibody are attracted to a magnet of a BF separator 14 to remove a R3 reagent containing non-reacting (free) labeled antibody. Furthermore, a light emitting substrate (R5 reagent) that emits light in the reaction process with the labeled antibody is added, and a light emitting amount generated through the reaction of the labeled antibody and the light emitting substrate is measured. After such processes, the antigen or the antibody contained in the specimen that bonds with the labeled antibody is quantitatively measured.

As shown in FIGS. 1 and 2, the immune analyzer 1 includes a measuring device 2, a specimen conveyance section (sampler) 3 arranged on the front surface side of the measuring device 2, and a control device 4 including PC (personal computer) electrically connected to the measuring device 2. The measuring device 2 is configured by a pipette chip supply device 30, an urgent specimen/chip conveyance section 20, a specimen dispensing arm 5, a nozzle wiping unit 16, reagent installing units 6 and 7, reagent dispensing arms 8, 9, and 10, a primary reaction unit 11 and a secondary reaction unit 12, a cuvette supplying unit 13, a BF separator 14, and a detector 15. As shown in FIG. 2, each mechanism (various dispensing arms, reagent installing unit 7, and the like) in the measuring device 2 are controlled by a control unit 2a arranged in the measuring device 2. The specimen conveyance section 3 is also controlled by the control unit 2a. In the immune analyzer 1 according to the present embodiment, the disposable pipette chip (not shown) is replaced every time aspiration and discharge of the specimen are performed to suppress specimen such as blood aspirated and discharged by the specimen dispensing arm 5 from mixing with other specimen. Each configuration of the measuring device will be described later.

As shown in FIG. 3, the control unit 2a is mainly configured by a CPU 2b, a ROM 2c, a RAM 2d, and a communication interface 2e.

The CPU 2b executes computer programs stored in the ROM 2c and the computer programs read by the RAM 2d. The ROM 2c stores computer programs to be executed by the CPU 2b, data used in executing the computer program, and the like. The RAM 2d is used to read out the computer program stored in the ROM 2c. In executing the computer program, the RAM 2d is used as a work region of the CPU 2b.

The communication interface 2e is connected to the control device 4, and transmits optical information (data of received light amount generated by reaction of the labeled antibody and light emitting substrate) of the specimen to the control device 4, and receives signals from the control unit 4a of the control device 4. The communication interface 2e also has a function of transmitting a command from the CPU 2b for driving each unit of the specimen conveyance section 3 and the measuring device 2.

As shown in FIG. 1, the specimen conveyance section 3 is configured to convey a rack 101 mounted with a plurality of test tubes 100 accommodating the specimen to a position corresponding to an aspirating position 1a at where the specimen dispensing arm 5 aspirates the specimen. The specimen conveyance section 3 includes a rack set part 3a for setting the rack 101 in which the test tubes 100 accommodating non-processed specimen are mounted, and a rack storing part 3b for storing the rack 101 in which the test tubes 100 accommodating the dispensing processed specimen are mounted. The test tube 100 accommodating the non-processed specimen is conveyed to a position corresponding to the aspirating position 1a of the specimen dispensing arm 5, so that the specimen dispensing arm 5 aspirates specimen such as blood in the test tube 100, and thereafter, the rack 101 mounted with the test tube 100 is stored in the rack storing part 3b. Each test tube 100 is attached with a barcode recorded with identifying information for identifying the accommodating specimen. The test tube 100 mounted in the tack 101 set in the rack set part 3a is conveyed to the aspirating position 1a after the respective identifying information is read by a barcode reader (not shown).

The control device 4 consists of a personal computer (PC), and includes a control unit 4a including CPU, ROM, RAM, a display unit 4b and a keyboard 4c. The display unit 4b is arranged to display result of analysis obtained by analyzing data of digital signals transmitted from a detector 15, user interface, and the like, and has an input function of a touch panel.

The configuration of the control device 4 will now be described using FIG. 4. The control device 4 is configured by a computer 401 mainly consisting of the control unit 4a, the display unit 4b, and the keyboard 4c. The control unit 4a is mainly configured by a CPU 401a, a ROM 401b, a RAM 401c, a hard disc 401d, a read-out device 401e, an input/output interface 401f, a communication interface 401g, and an image output interface 401h. The CPU 401a, the ROM 401b, the RAM 401c, the hard disc 401d, the read-out device 401e, the input/output interface 401f, the communication interface 401g, and the image output interface 401h are connected by a bus 401i.

The CPU 401a executes computer programs stored in the ROM 401b and the computer programs loaded in the RAM 401c. The computer 401 serves as the control device 4 when the CPU 401a executes the application program 404a, as hereinafter described.

The ROM 401b is configured by mask ROM, PROM, EPROM, EEPROM, and the like, and is recorded with computer programs to be executed by the CPU 401a, data used for the same, and the like.

The RAM 401c is configured by SRAM, DRAM, and the like. The RAM 401c is used to read out the computer programs recorded on the ROM 401b and the hard disc 401d. The RAM 401c is used as a work region of the CPU 401a when executing the computer programs.

The hard disc 401d is installed with various computer programs to be executed by the CPU 401a such as operating system and application program, as well as data used in executing the computer program. The application program 404a related to immune analysis and maintenance of the apparatus according to the present embodiment is also installed in the hard disc 401d.

The read-out device 401e is configured by flexible disc drive, CD-ROM drive, DVD-ROM drive, and the like, and is able to read out computer programs and data recorded on a portable recording medium 404. The immune analysis application program 404a is stored in the portable recording medium 404, where the computer 401 reads out the application program 404a from the portable recording medium 404, and installs the application program 404a to the hard disc 401d.

The application program 404a is not only provided by the portable recording medium 404, but also provided through communication line (wired or wireless) from external devices communicatably connected with the computer 401 through the communication line. For instance, the application program 404a may be stored in the hard disc of the server computer on the Internet, so that the computer 401 can access the server computer to download the application program 404a and install the application program 404a to the hard disc 401d.

Operating system providing graphical user interface environment such as Windows (registered trademark) manufactured and sold by US Microsoft Co. is installed in the hard disc 401d. In the following description, the application program 404a according to the present embodiment is assumed to operate on the operating system.

The input/output interface 401f is configured by serial interface such as USB, IEEE1394, RS-232C; parallel interface such as SCSI, IDE, IEEE1284; analog interface such as D/A converter, A/D converter, and the like. The keyboard 4c and a mouse (not shown), and the display unit 4b having a touch panel function are connected to the input/output interface 401f, so that the user can input data to the computer 401 using the keyboard 4c or the mouse. The user can input to the computer 401 by touching the display unit 4b.

The communication interface 401g is, for example, Ethernet (registered trademark) interface. The computer 401 transmits and receives data with the measuring device 2 using a predetermined communication protocol by means of the communication interface 401g.

The image output interface 401h is connected to the display unit 4b configured by LCD, CRT, or the like, and is configured to output an image signal corresponding to the image data provided from the CPU 401a to the display unit 4b. The display unit 4b displays the image (screen) according to the input image signal.

The immune analysis application program 404a installed in the hard disc 401d of the control unit 4a measures the amount of antigen in the measurement sample using the light emitting amount (data of digital signal) of the measurement sample transmitted from the detector 15 of the measuring device 2.

Each configuration of the measuring device 2 will now be described using FIG. 1.

As shown in FIG. 1, the pipette chip supply device 30 has a function of supplying a great amount of pipette chips accommodated in the chip accommodating part (not shown) to the urgent specimen/chip conveyance 20 one at a time.

The urgent specimen/chip conveyance section 20 is configured to convey the test tube 102 containing an urgent specimen that needs to cut into the specimen being conveyed by the specimen conveyance section 3 and be tested to the attachment position 1b (see FIG. 1) of the pipette chip of the specimen dispensing arm 5. The urgent specimen/chip conveyance section 20 is configured to convey the pipette chip received from the pipette chip supply device 30 to the attachment position 1b of the specimen dispensing arm 5.

The specimen dispensing arm 5 has a function of dispensing the specimen in the test tube 100 conveyed to the aspirating position 1a (see FIG. 1) by the specimen conveyance section 3 or the specimen in the test tube 102 conveyed to the attachment position 1b by the urgent specimen/chip conveyance section 20 to a cuvette held by a holder 11b of a rotatable table 11a of the primary reaction unit 11 to be hereinafter described. The specimen dispensing arm 5 includes a motor 51, a drive transmission part 52 connected to the motor 51, an arm 54 attached to the drive transmitting part 52 by way of a shaft 53, an arm supporting part 56 for supporting the arm 54, and a horizontal drive mechanism 56 for moving the arm supporting part 56 in the horizontal direction. The drive transmitting part 52 is configured to turn the arm 54 with the shaft 53 as the center by the driving force from the motor 51, and move the arm in the up and down direction (Z direction).

The arm 54 has a nozzle (not shown), and the pipette chip conveyed by the conveyance rack 23 (see FIG. 1) of the urgent specimen/chip conveyance section 20 is attached to the distal end of the nozzle.

The chip separation unit 140 is arranged to separate the pipette chip attached to the specimen dispensing arm 5. The chip separation unit 140 includes a release strip that contacts the upper edge of the pipette chip and separates the pipette chip from the specimen dispensing arm, and a chip accommodating part (not shown) for accommodating the separated pipette chip.

The reagent installing unit 6 is arranged to install the reagent bin in which an R1 reagent containing trapped antibody is accommodated and a reagent bin in which a R3 reagent containing labeled antibody is accommodated. The reagent installing unit 7 is arranged to install a reagent bin in which an R2 reagent containing magnetic particles is accommodated. The cuvette supplying unit 13 is configured to sequentially supply a plurality of cuvettes (not shown) to the holder 11b of the rotatable table 11a of the primary reaction unit 11.

The primary reaction unit 11 is arranged to rotatably transfer the cuvette held by the holder 11b of the rotatable table 11a by a predetermined angle for every predetermined period, and to stir the specimen, the R1 reagent, and the R2 reagent in the cuvette. The primary reaction unit 11 includes a specimen conveying part 11c for conveying the cuvette accommodating the R1 reagent and the R2 reagent to the BF separator 14 to be hereinafter described.

The reagent dispensing arm 8 has a function of aspirating the R1 reagent in the reagent bin installed in the reagent installing unit 6 and dispensing the aspirated R1 reagent into the cuvette dispensed with specimen of the holder 11b of the rotatable table 11a of the primary reaction unit 11.

The reagent dispensing arm 9 has a function of dispensing the R2 reagent in the reagent bin installed in the reagent installing unit 7 into the cuvette dispensed with the specimen and the R1 reagent of the primary reaction unit 11.

The BF separator 14 has a function of separating the non-reacting R1 reagent (unnecessary component) and the magnetic particles from the sample in the cuvette conveyed by the container conveying part 11c of the primary reaction unit 11, and a function of separating the non-reacting R3 reagent (unnecessary component) and the magnetic particles from the sample in the cuvette conveyed by the container conveying part 12c of the secondary reaction unit 12. The cuvette of the BF separator 14 separated with non-reacting R1 reagent and the like is conveyed to the holder 12b of the rotatable table 12a of the secondary reaction unit 12 by a conveyance catcher unit (not shown).

The secondary reaction unit 12 has a configuration similar to the primary reaction unit 11, and is arranged to rotatably transfer the cuvette held by the holder 12b of the rotatable table 12a by a predetermined angle for every predetermined period, and to stir the specimen, the R1 reagent, the R2 reagent, the R3 reagent, and the R5 reagent in the cuvette. The second reaction unit 12 includes a specimen conveying part 12c for conveying the cuvette accommodating the stirred specimen and the like to the BF separator 14. The specimen conveying part 12c has a function of conveying the cuvette processed by the BF separator 14 again to the holder 12b of the rotatable table 12a.

The reagent dispensing arm 10 has a function of aspirating the R3 reagent in the reagent bin installed in the reagent installing unit 6, and dispensing the aspirated R3 reagent into the cuvette dispensed with the specimen, the R1 reagent, and the R2 reagent of the primary reaction unit 11. The reagent dispensing arm 10 has a function of dispensing the R5 reagent containing light emitting substrate in the reagent bin (not shown) installed at the lower part of the immune analyzer 1 to the cuvette accommodating the specimen, the R1 reagent, the R2 reagent, and the R3 reagent of the secondary reaction unit 12.

The detector 15 is arranged to measure the amount of antigen contained in a specimen by detecting the light generated in the reaction process of the labeled antibody bound to the antigen of the specimen performed with a predetermined process and the light emitting substrate with a photo multiplier tube.

In order to smoothly operate the measuring device 2 configured as above, and exhibit the predetermined performance, the user needs to perform various maintenances. In the present embodiment, the schedule of the relevant maintenance is stored in the hard disc 401d of the control device 4, and the schedule of the stored maintenance is displayed on the display unit 4b (see FIG. 1 and FIG. 4). In this case, the schedule of the maintenance is displayed on the display unit 4b in a "calendar format" in which the dates are displayed in a list according to the type. The user can perform various maintenances while checking the schedule of the maintenance displayed on the display unit 4b.

The "calendar format" is a format in which the dates for one month, where one row is sectionalized in units of one week as in seven days of the week, are displayed in a list, and the non-performed maintenance name is displayed under the respective date. That is, the dates or the weeks are displayed in a list, and the performance status of the maintenance is displayed in correspondence to each date. Such calendar format is convenient in checking the schedule of maintenance. Not limited to displaying one month in a list, the dates for one to two weeks may be displayed in a list, for example.

The maintenance operation of the immune analyzer 1 according to the present embodiment will now be described based on the drawings.

The hard disc 401d arranged in the control unit 4a of the control device 4 is stored with a computer program (one part of application program 404a) related to the maintenance of the measuring device 2 according to the embodiment. The computer program is read out from the hard disc 401d, loaded to the RAM 401c, and executed by the CPU 401a.

The computer program of the maintenance operation according to the embodiment is stored in the ROM 2c (see FIG. 3) arranged in the control unit 2a of the measuring device 2. The computer program is read out from the ROM 2c, loaded to the RAM 2d, and executed by the CPU 2b.

[To Display of Maintenance Schedule Screen]

Figure 6:
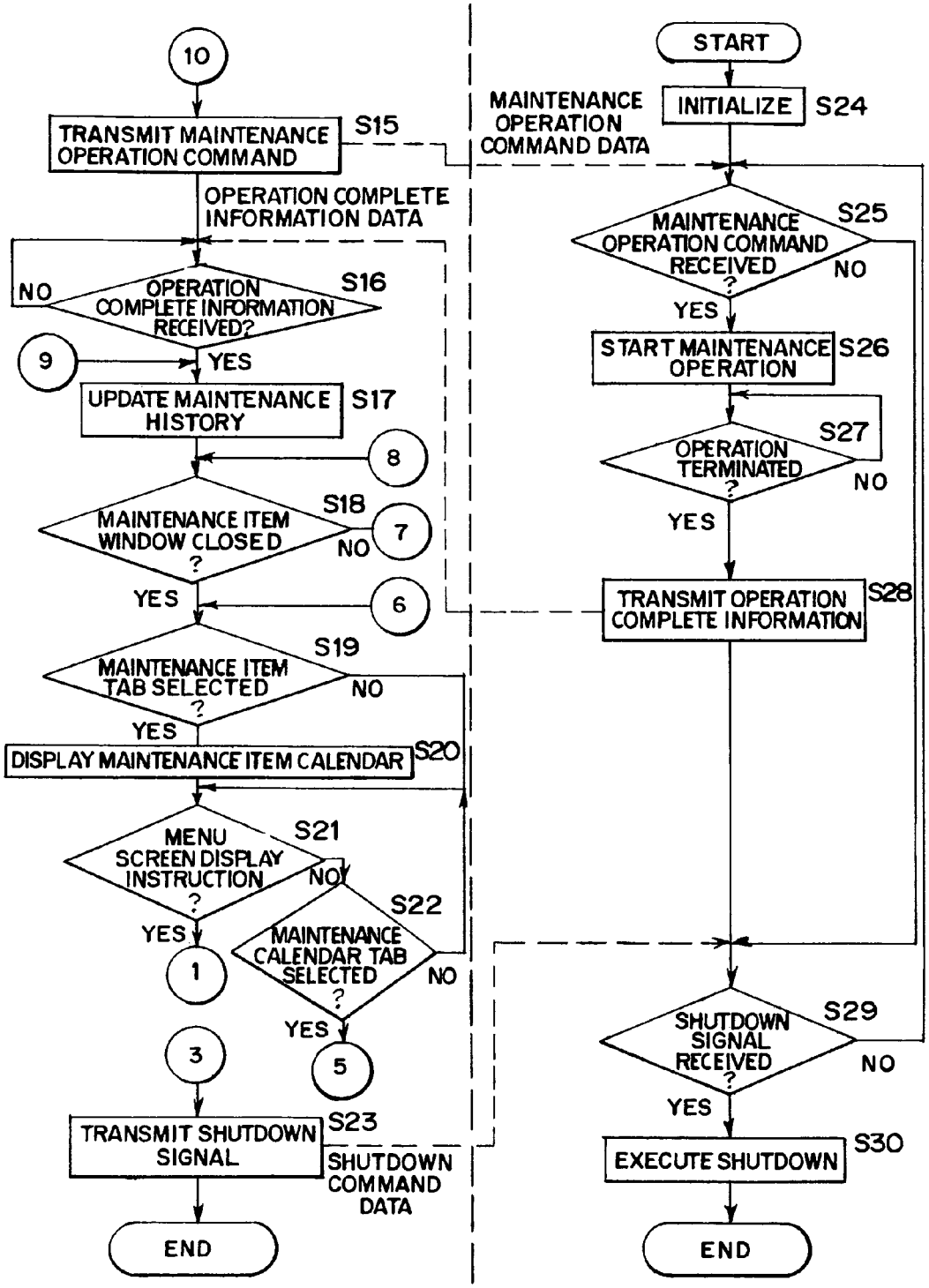
FIG. 6 is a flowchart showing a maintenance operation of the immune analyzer shown in FIG. 1.

As shown in FIG. 6, when the power (not shown) of the measuring device 2 is turned ON, initialization of the control unit 2a (initialization of program) is performed, the operation check of each unit of the measuring device 2 is performed, and the standby state of the measuring device 2 (see FIG. 1 to FIG. 3) is obtained in step S24.

Figure 5:
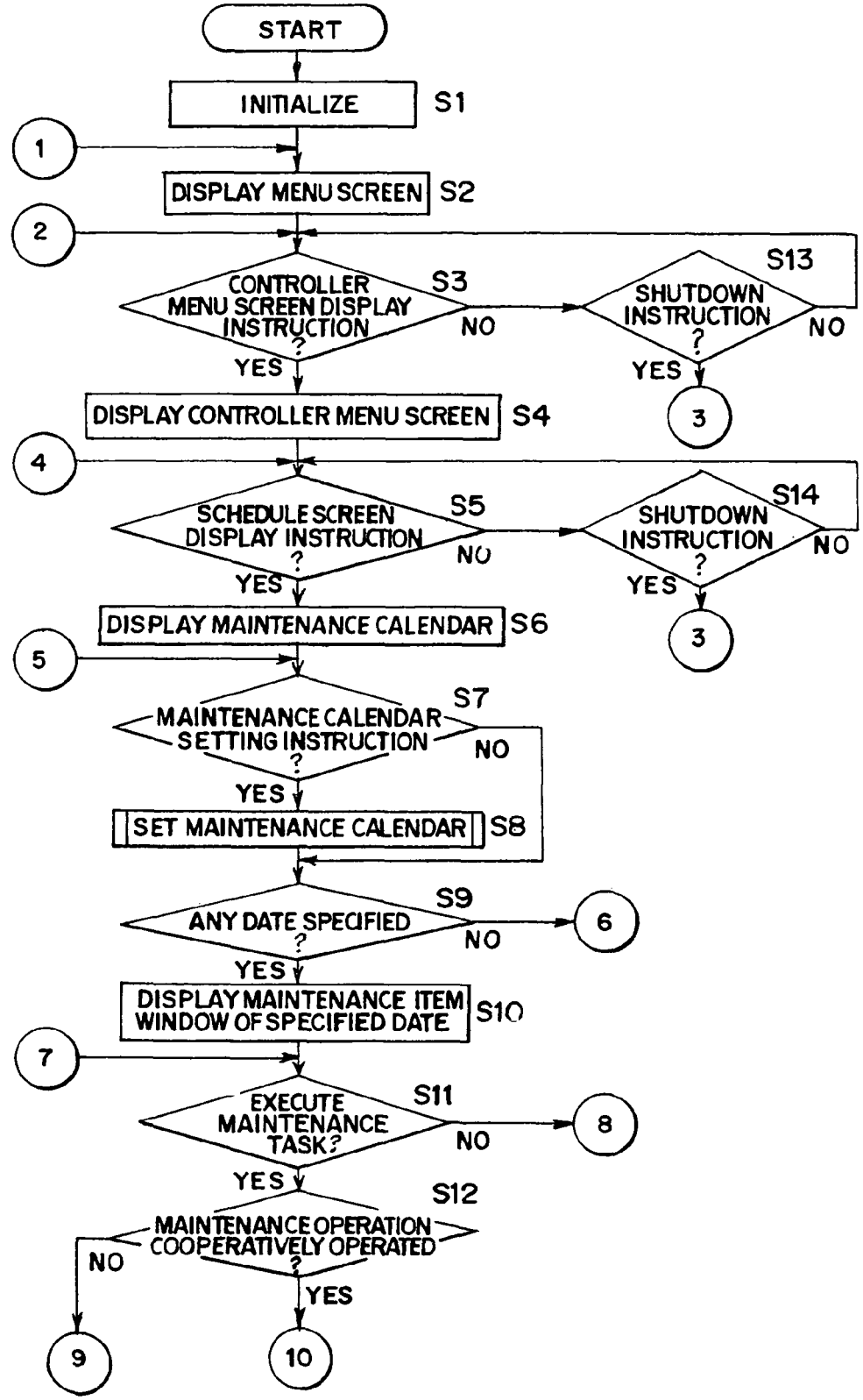
FIG. 5 is a flowchart showing a maintenance operation of the immune analyzer shown in FIG. 1.

When the power (not shown) of the control device 4 (computer 401) is turned ON as shown in FIG. 5, in step S1, initialization of the control device 4 (initialization of program) is performed, and a menu screen is displayed on the display unit 4b (step S2).

Figure 7:
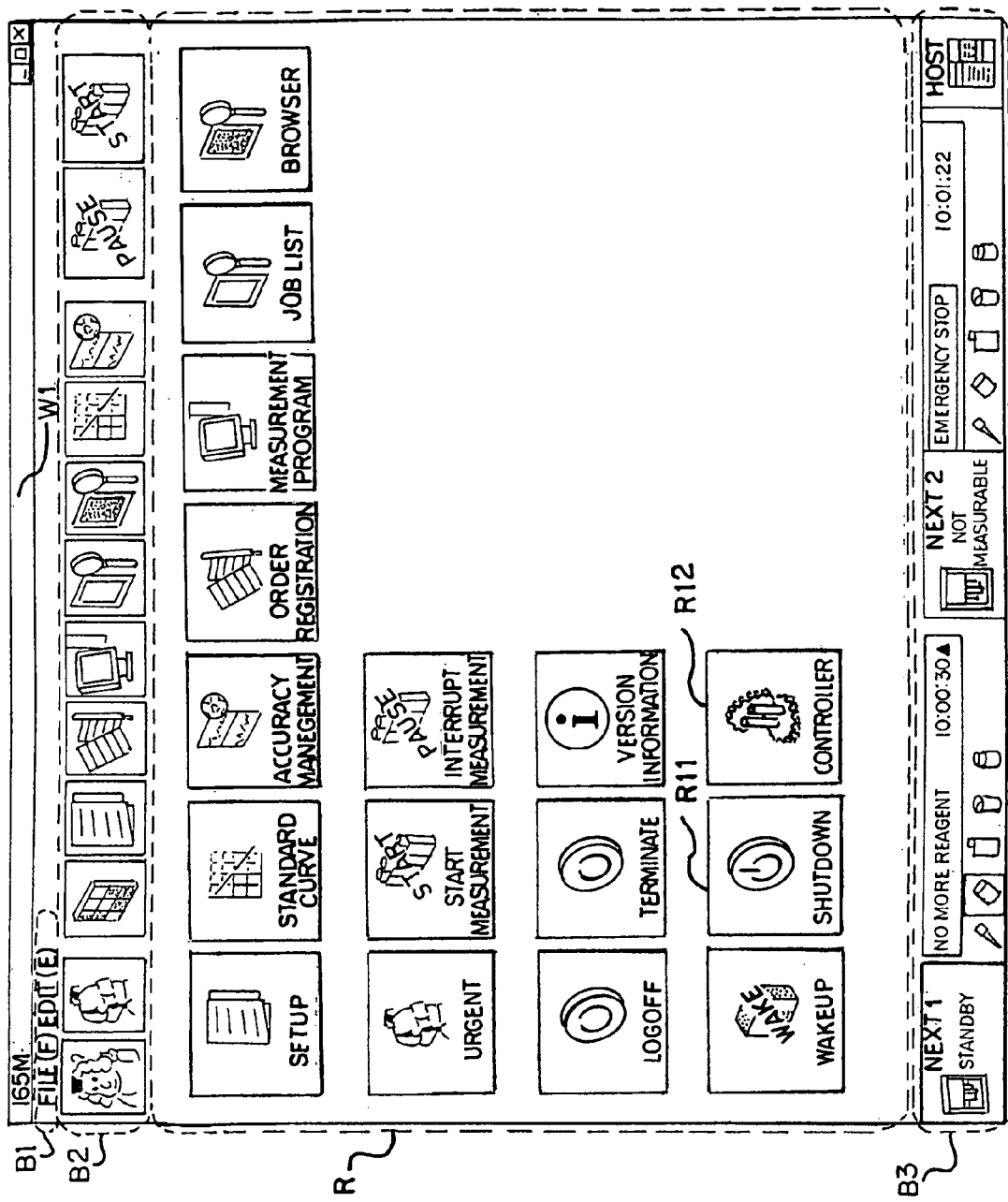
FIG. 7 is a view showing an operation screen (menu screen) displayed on the display unit of the control device shown in FIG. 1.

FIG. 7 is a view showing a menu screen W1 displayed on the display unit 4b. As shown in FIG. 7, the menu screen W1 has a menu bar B1, a tool bar B2, a function display region R, and a status bar B3. In the menu bar B1, a route menu in the operation screen is displayed. In the respective route menu, a sub-menu exists, and a pull-down menu can be displayed by the input of a mouse (not shown) or a keyboard 5c. A plurality of tool button icons for executing functions having high usage frequency in the menu screen W1 is displayed on the tool bar B2. The status bar B3 is a region for displaying the storage stock state in the apparatus of the pipette chip, cuvette, reagent etc., which are consumable goods, and the abnormal state of the apparatus when measuring device 2 is used.

In the function display region R, shortcut buttons for the operation of the measuring device 2 of screen transition, standard curve measurement of the measuring device 2, accuracy management, specimen measurement, and the like are displayed. In the present embodiment, in the function display region R of the menu screen W1, a "shutdown" button R11 for shutting down the control device 4 (computer 401) and the measuring device 2, a "controller button" R12 for transitioning to the screen arranged with the shortcut button of the operation for operating the specimen analyzer, and the like are arranged.

Figure 8:
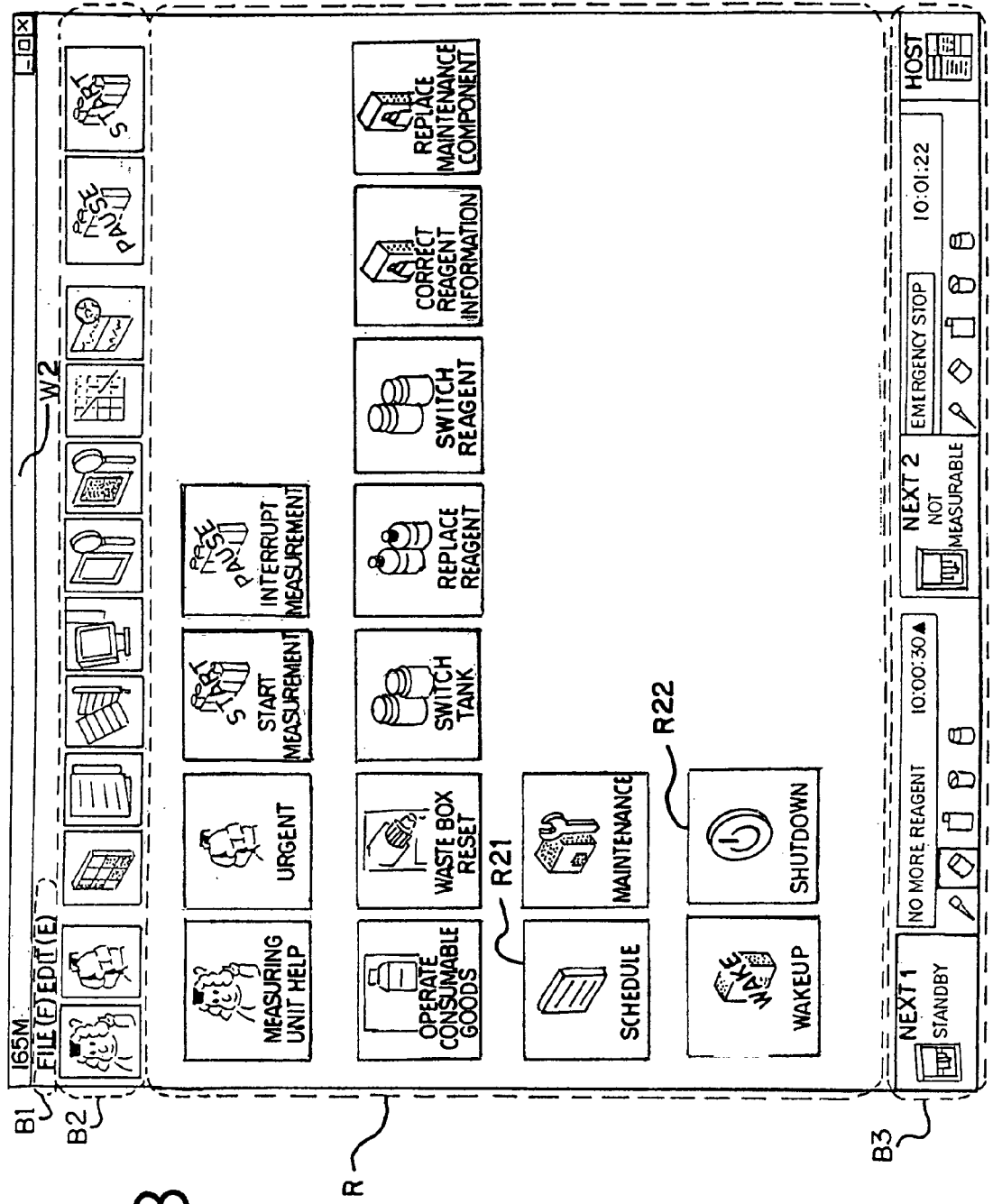
FIG. 8 is a view showing an operation screen (controller menu screen) displayed on the display unit of the control device shown in FIG. 1.

Among the shortcut buttons of the menu screen W1, if the controller button R12 is selected (Yes in step S3), a controller menu screen W2 shown in FIG. 8 is displayed on the display unit 4b (step S4). In this controller menu screen W2, the content displayed in the menu bar B1, the tool bar B2, and the status bar B3 are the same as the menu screen W1 described above.

As shown in FIG. 8, the shortcut buttons related to the operation (replacement, maintenance etc. of consumable goods) of the measuring device 2 are displayed in the function display region R of the controller menu screen W2. In the present embodiment, a "schedule button" R21 for checking the maintenance schedule of the measuring device 2, a "shutdown button" R22 for shutting down the measuring device 2 and the control device 4 (computer 401), and the like are arranged in the function display region R.

[Display of Maintenance Schedule Screen]

Figure 9:
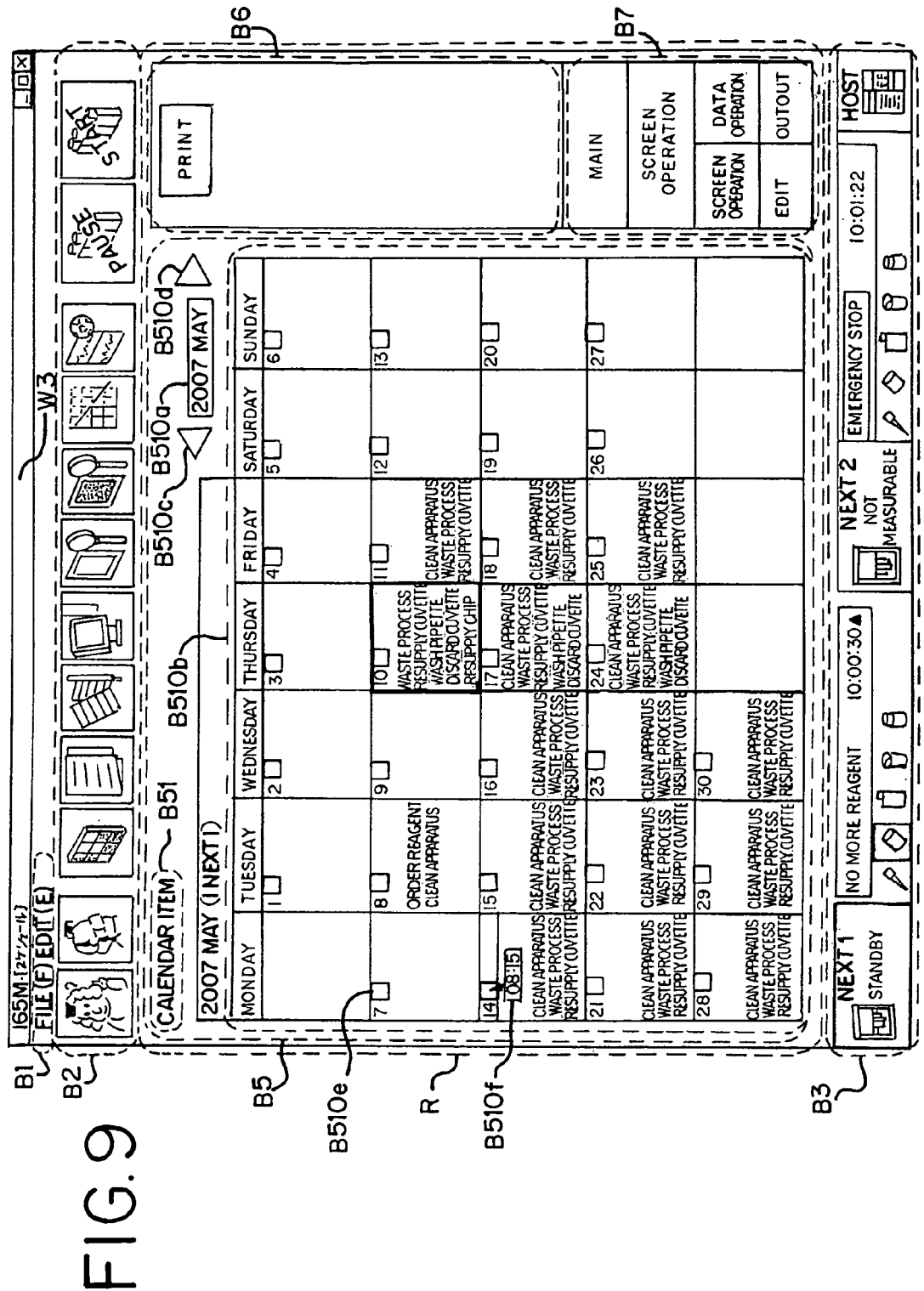
FIG. 9 is a view showing a maintenance item scheduled to be performed in the immune analyzer shown in FIG. 1 in a calendar format.

Among the shortcut buttons of the controller menu screen W2, if the schedule button R21 is selected (Yes in step S5), a schedule menu screen W3 shown in FIG. 9 is displayed on the display unit 4b (step S6).

As shown in FIG. 9, the function display region R of the schedule menu screen W3 includes a calendar display region B5 for calendar displaying the schedule of the maintenance of the measuring device 2, an operation panel execution button region B6 for displaying the shortcut button of the route menu displayed on the menu bar B1, and an operation panel selection button region B7 for displaying the button for switching the button groups displayed on the operation panel execution button region B6.

Figure 10:
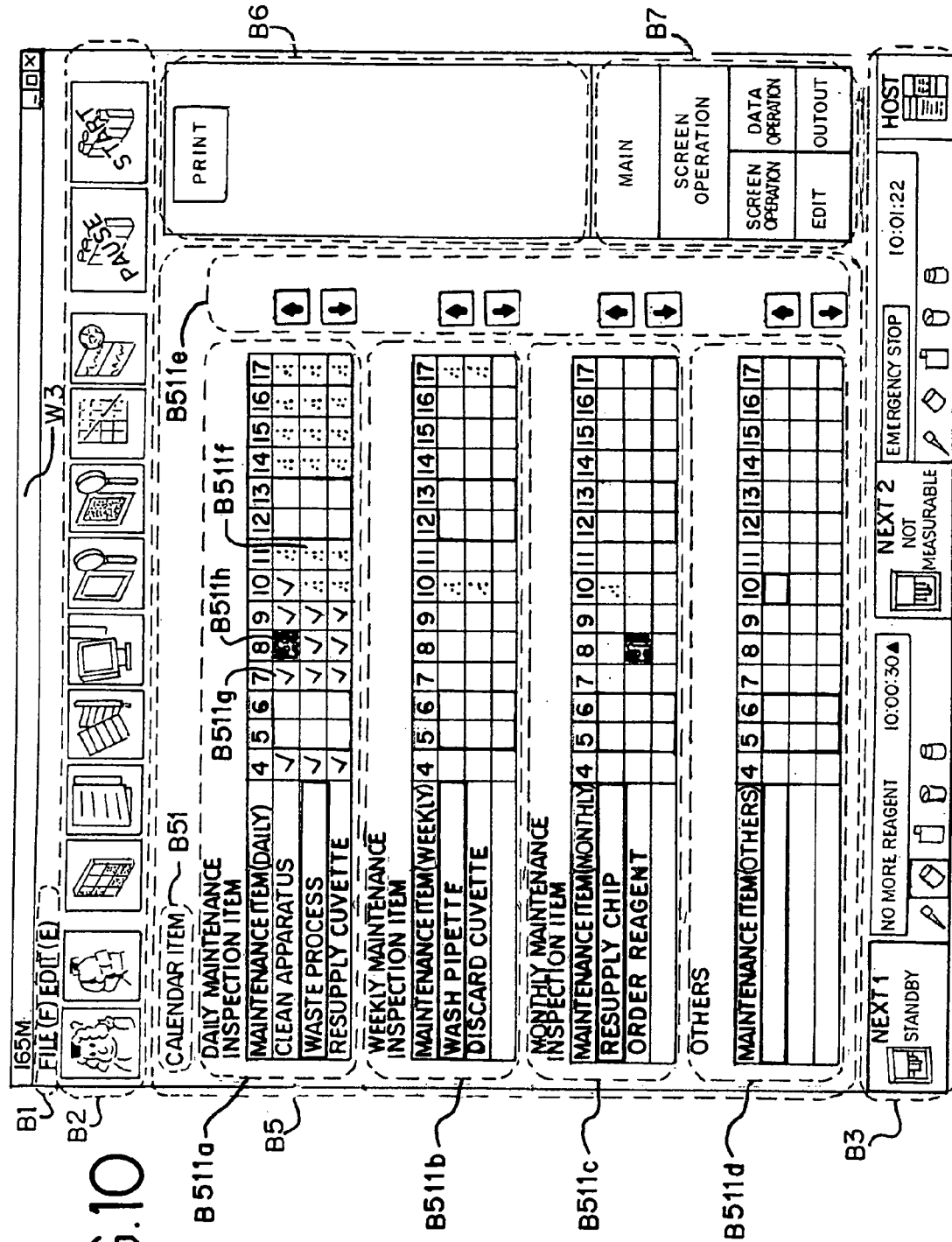
FIG. 10 is a view displaying the maintenance item to be performed in the immune analyzer shown in FIG. 1 by items.

A display calendar selecting part B51 including a tab for selecting the type of calendar to display is arranged in the calendar display region B5. The display calendar selecting part B51 includes a calendar display tab for displaying the maintenance item of the performing schedule of the measuring device 2 in a calendar format, and an item display tab for displaying the maintenance item of the measuring device 2 by maintenance cycle. If the item display tab is selected, the calendar for the maintenance item shown in FIG. 10 is displayed in the calendar display region B5 of the schedule menu screen W3.

The calendar display region B5 is arranged with a calendar year and month display unit B510a for displaying "year and month" of the calendar for displaying the maintenance item scheduled to be performed, a calendar display part B510b for displaying a calendar displaying a calendar of "year and month" displayed in the calendar year and month display unit B510, a previous month display button c for displaying a calendar of the previous month on the calendar display part B510b, and a next month display button B510d for displaying a calendar of the next month on the calendar display part B510b.

The dates for one month sectionalized by a grid line are displayed for every seven days of the week in the calendar display part B510b. The maintenance item not yet performed in the immune analyzer 1 is text displayed in the grid of each date. Furthermore, when the immune analyzer 1 is automatically activated, and a standby time (hereinafter referred to as wake up time) when a measurement standby state in which measurement can be performed is obtained is set, a wakeup icon B510e is displayed on the calendar display part B510b. When the wakeup time is set, the immune analyzer 1 is activated a predetermined time before (e.g. 30 minutes before) the standby time. The predetermined time is a time necessary until the standby state is obtained from when the immune analyzer 1 is activated, and during this time, the initial operation (e.g., origin adjustment of the motor of each unit, temperature adjustment such as heating of the detector 15, cooling of the reagent installing unit 6 and the reagent installing unit 7, and the like) of the immune analyzer 1 is performed. Saturday and Sunday are set as default holidays. The setting etc. of the maintenance item, the performing cycle thereof, holidays, and wakeup time displayed on the calendar display part B510b (calendar display region B5) are set in the maintenance calendar setting (step S8). When set as the maintenance items to be performed every day in the maintenance calendar setting, the maintenance item scheduled to be performed every time is text displayed in the grid of the date other than holidays as shown in FIG. 9.

When the cursor of the mouser (not shown) overlaps the wakeup icon B510e, a pop up window B510f displaying the wakeup time at the date specified by the cursor is displayed. Furthermore, when the wakeup icon B510e is clicked, a wakeup time change dialogue for individually changing the wakeup time is displayed. The user inputs the desired wakeup time to the wakeup time change dialogue to change the reference wakeup time set in the maintenance calendar setting for every date. The details of changing the wakeup time will be described hereinafter.

The maintenance calendar setting (step S8) is executed by selecting "customize" from the submenu of "screen operation" (D) (Yes in step S7) in the menu displayed on the menu bar B1 ("file" (F) and "edit" (E)) when the schedule menu screen W3 is displayed on the display unit 4b. The setting of the maintenance calendar will be described in detail hereinafter.

[Perform Maintenance Task]

Figure 11:
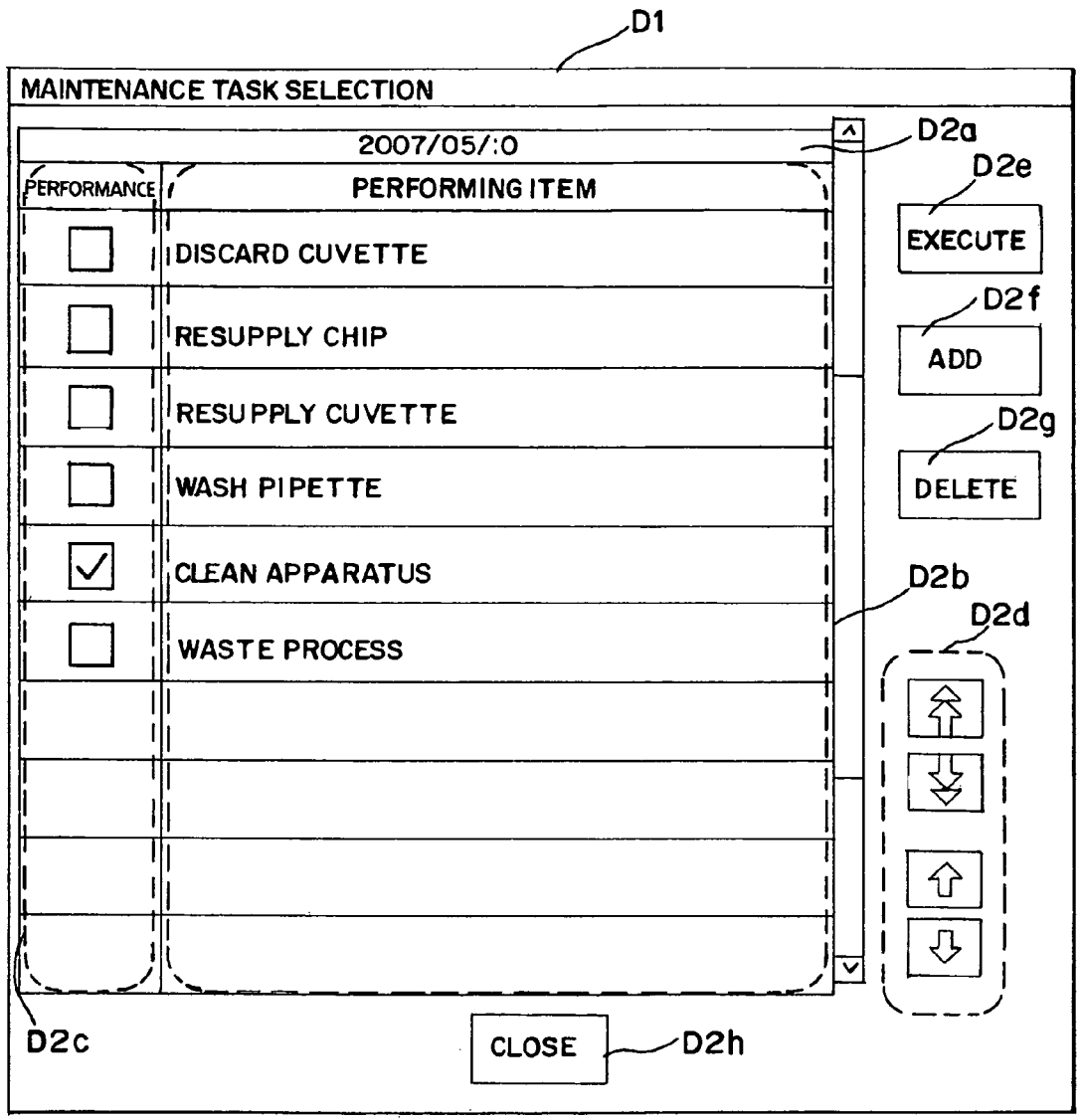
FIG. 11 is a view showing a dialogue window displayed when a predetermined date is specified in a calendar shown in FIG. 9.

When the grid of May 10 is selected of the grid (frame) displaying the date of the calendar displayed on the calendar display part B510b in step S9 (Yes in step S9), a maintenance task selection dialogue D1 performed on a specified date as shown in FIG. 11 is displayed overlapping the front surface of the schedule menu screen W3 (step S10). If the grid (frame) is not selected (No in step S9), the process proceeds to step S19. In the present embodiment, May 10, 2007 is set as the date the operator operates the apparatus.

As shown in FIG. 11, the maintenance task selection dialogue D1 includes a specified date display part D2a for displaying the specified date, a maintenance item display part D2b for displaying the list of maintenance item scheduled to be performed or already performed on the specified date, a check box display part D2c for checking whether or not the maintenance item displayed on the maintenance item display part D2b has been performed, and a scroll button display region D2d displaying a scroll button for moving in the up and down direction the cursor for selecting one of the maintenance items displayed on the maintenance item display part D2b. In FIG. 11, "resupply chip" is selected with the cursor from the maintenance items.

In the maintenance task selection dialogue D1, "execute" button D2e for executing the maintenance item, "add" button D2f for adding the maintenance item to perform, "delete" button D2g for deleting the maintenance item not to be performed from the list of maintenance items to be performed on the specified date, and "close" button D2h for terminating the maintenance task selection dialogue D1 are arranged.

In the present embodiment, in the maintenance setting to be hereinafter described, "discard cuvette", "resupply chip", "resupply cuvette", and "waste process" which are maintenance items newly added by the user; "pipette washing" which is a maintenance item set in the apparatus as a default in advance and involves maintenance operation; and "clean apparatus" which is a maintenance item set in the apparatus as a default in advance but does not involve maintenance operation are displayed in the performing maintenance item display part D2b.

When performing the displayed maintenance item, the maintenance item desired to be performed is first selected with a cursor using a scroll button. The selected performing item is displayed in blue (hatching display in the figure), where when the user pushes the "execute" button D2e (Yes in step S11), the CPU 401a determines whether or not the maintenance item to be performed involves maintenance operation (step S12).

[Case where Performed Maintenance Item Involves Maintenance Operation]

If the executed maintenance item involves maintenance operation (in the present embodiment, "pipette washing") (Yes in step S12), the CPU 401a of the control device 4 transmits a maintenance operation start command to the control unit 2a of the measuring device 2 (step S15).

On the other hand, the CPU 2*b* of the measuring device 2 determines whether or not the maintenance operation start command is received (step S25). If the command is received (Yes in step S25), the CPU 2*b* controls the mechanism so that the mechanism starts the maintenance operation according to a predetermined sequence (step S26).

The CPU 2*b* determines whether or not the predetermined maintenance operation is completed in step S27, and transmits the maintenance operation complete information to the control unit 4*a* of the control device 4 (step S28) if the maintenance operation is completed (Yes in step S27).

The CPU 401*a* of the control device 4 transmits the maintenance operation start command to the control unit 2*a* of the measuring device 2, and thereafter determines whether or not the maintenance operation complete information is received in step S16.

If the maintenance operation complete information is received (Yes in step S16), the CPU 401*a* updates the maintenance history (step S17). Specifically, the maintenance item involving the performed maintenance operation and the date and the log in user name are stored in the hard disc 401*d* in correspondence to each other, a check is displayed on the check box of the maintenance item displayed on the maintenance task selection dialogue D1, and the relevant maintenance item is erased from the calendar display part B510*b*.

[Case where Performed Maintenance Item does not Involve Maintenance Operation]

If the executed maintenance item does not involve maintenance operation in step S12 of FIG. 5 ("discard cuvette" "resupply chip", "resupply cuvette", "clean apparatus", and waste process" of the maintenance items shown in FIG. 11) (No in step S12), the CPU 401*a* updates the history of the performed maintenance item (step S17). Specifically, the performed item and the date and the log in user name are stored in the hard disc 401*d* in correspondence to each other, a check is displayed on the check box of the maintenance item (see FIG. 11) displayed on the maintenance task selection dialogue D1, and the relevant maintenance item is erased from the calendar display part B510*b*.

In step S18, the CPU 401*a* determines whether or not the "close" button D2*h* for terminating the maintenance task selection dialogue D1 is pushed. When the "close" button D2*h* is pushed by the user (Yes in step S18), the maintenance task selection dialogue D1 is terminated, and the process returns to step S11. The schedule menu screen W3 is displayed on the display unit 4*b* when the maintenance task selection dialogue D1 is closed.

[Item Calendar Display]

In step S19, the CPU 401*a* determines whether or not the item display tab of the schedule menu screen W3 is selected. When the item display tab is selected, the calendar of the maintenance item shown in FIG. 10 is displayed on the calendar display region B5 of the schedule menu screen W3 displayed on the display unit 4*b* (step S20).

As shown in FIG. 10, the item display tab has four display regions according to the type of maintenance. That is, the item display tab includes "Daily maintenance inspection item" display region B511*a* that is normally performed every apparatus operation day, "Weekly maintenance inspection item" display region B511*b* that is performed every week, "Monthly maintenance inspection item" display region B511*c* that is performed every month, maintenance item "Others" display region B511*d* that is performed as necessary or which cycle is not set, and movement button display region B511*e* for moving the cursor up and down for selecting the maintenance item displayed on each display region.

The "Daily maintenance inspection item", "Weekly maintenance inspection item", "Monthly maintenance inspection item", and "Others" are displayed based on the setting of the cycle of the maintenance item set in the calendar display setting of step S8, and the history of the maintenance is recorded in a calendar format described above.

In the present embodiment, "clean apparatus" for cleaning the periphery of the measuring device 2, "waste process" of processing the waste in the waste tank storing the waste used in the measuring device 2, and "resupply cuvette" for resupplying a cuvette which is one consumable good used in the measuring device 2 are displayed as the "Daily maintenance inspection item".

"Pipette washing" for intensified washing (washing with intensified washing degree performed separate from the washing performed in time of measurement of each specimen) all the dispensing arms (reagent dispensing arms 8, 9, and 10) of the measuring device 2, and "discard cuvette" for discarding the cuvette collected in the cuvette waste box (not shown) after the termination of the measurement are displayed as the "Weekly maintenance inspection item".

"Resupply chip" for supplying the pipette chip to the pipette chip supply device 30 and "order reagent" for ordering reagent to be used in the measuring device 2 are displayed as the "Monthly maintenance inspection item".

In each maintenance inspection item, a performed status mark is displayed on each date. In the present embodiment, a maintenance item scheduled to be performed icon B511*f* of a spanner or a working tool is displayed for the maintenance item scheduled to be performed; and a performed maintenance item icon B511*g* of a check mark is displayed for the maintenance item which performance is completed. Furthermore, displayed is a non-performed maintenance item icon B511*h* in which the box of the maintenance item scheduled to be performed B511*f* is reverse displayed in red (hatching in the figure) for items that are not performed and the scheduled day has elapsed. The user can easily check whether or not the maintenance item scheduled to be performed is executed by displaying the history of maintenance in a list by maintenance item, and the item that has not been performed with maintenance can be recognized at once.

[Shutdown Operation]

In steps S21, the CPU 401*a* determines whether or not an icon for displaying the menu screen W1 on the display unit 4*b* is selected of the tool buttons displayed on the tool bar B2 of the schedule menu screen W3. If the icon for displaying the menu screen W1 is selected (Yes in step S21), the CPU 401*a* returns the process to step S2 and displays the menu screen W1 on the display unit 4*b*. The CPU 401*a* determines whether or not a shutdown button R11 of the menu screen W1 is selected (step S13), and transmits shutdown command data to the CPU 2*b* of the measuring device 2 when the shutdown button R11 is selected (Yes in step S13) (step S23). The CPU 2*b* of the measuring device 2 determines whether or not the shutdown command data is received in step S29. If the shutdown command data is received (Yes in step S29), the CPU 2*b* executes the shutdown operation of the measuring device 2 (step S30).

If the icon for displaying the menu screen W1 on the display unit 4*b* is not selected (No in step S21), and if the CPU 401*a* further determines whether or not the calendar display tab is selected in step S22 and the calendar display tab is selected (Yes in step S22), the process returns to step S7, and if the calendar display tab is not selected (No in step S22), the process returns to step S21.

The shutdown operation can be executed when the controller menu screen W2 is displayed on the display unit 4b as well.

As shown in FIG. 5, when the controller menu screen W2 is displayed on the display unit 4b (No in step S5), the CPU 401a determines whether or not the shutdown button R22 is selected in step S14. If the shutdown button R22 is selected, the CPU 401a proceeds the process to step S23 of FIG. 6, and transmits the shutdown command data to the control unit 2a of the measuring device 2. The CPU 2b determines whether or not the shutdown command data is received in step S29. If the command is received (Yes in step S29), the CPU 2b executes the shutdown operation of the measuring device 2 in step S30.

[Setting of Display Condition of Calendar to be Displayed on Calendar Display Region B5]

Figure 12:
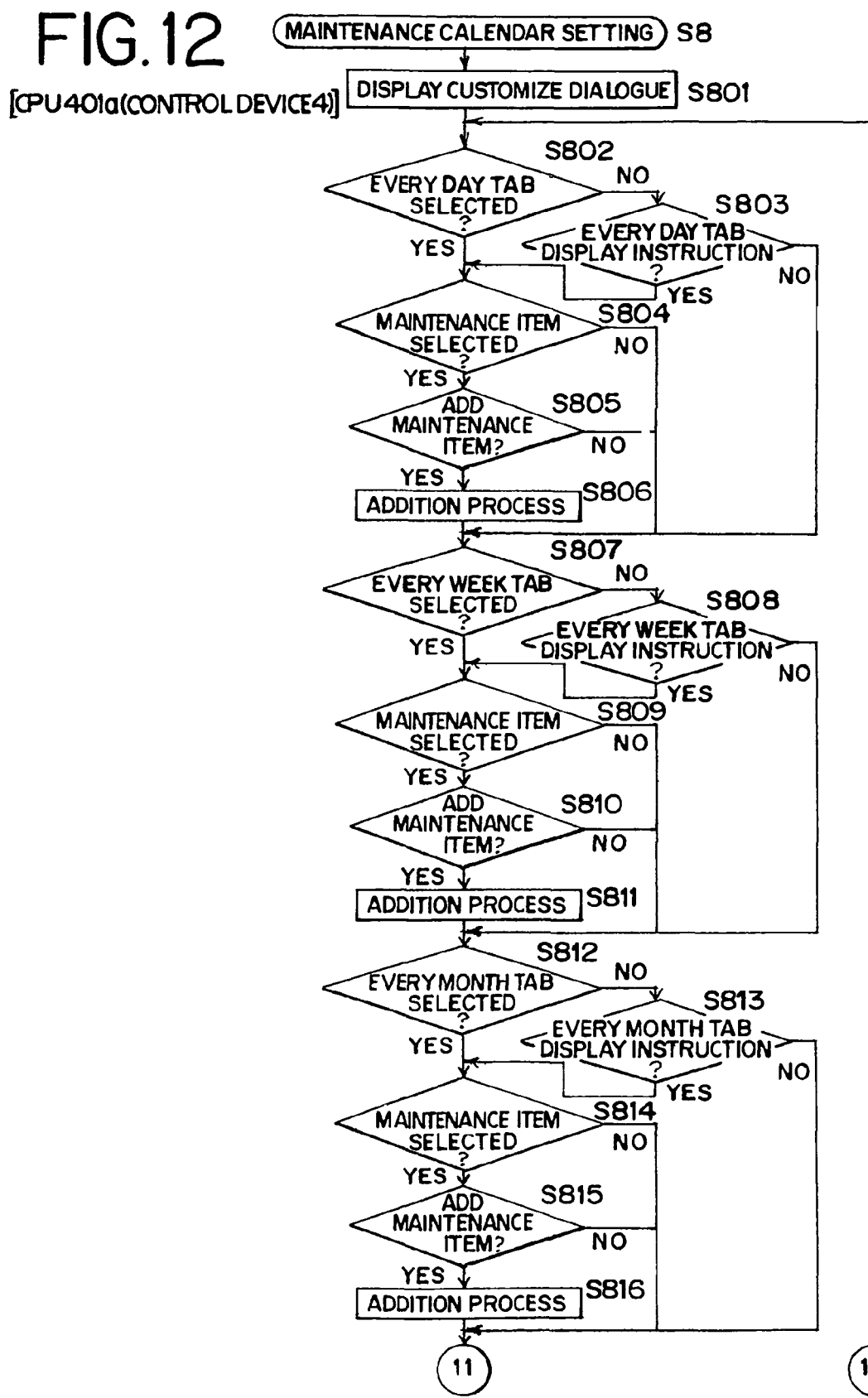
FIG. 12 is a sub-routine for describing a process for setting a display condition of a calendar display executed in step S8 of the flowchart shown in FIG. 5.
Figure 13:
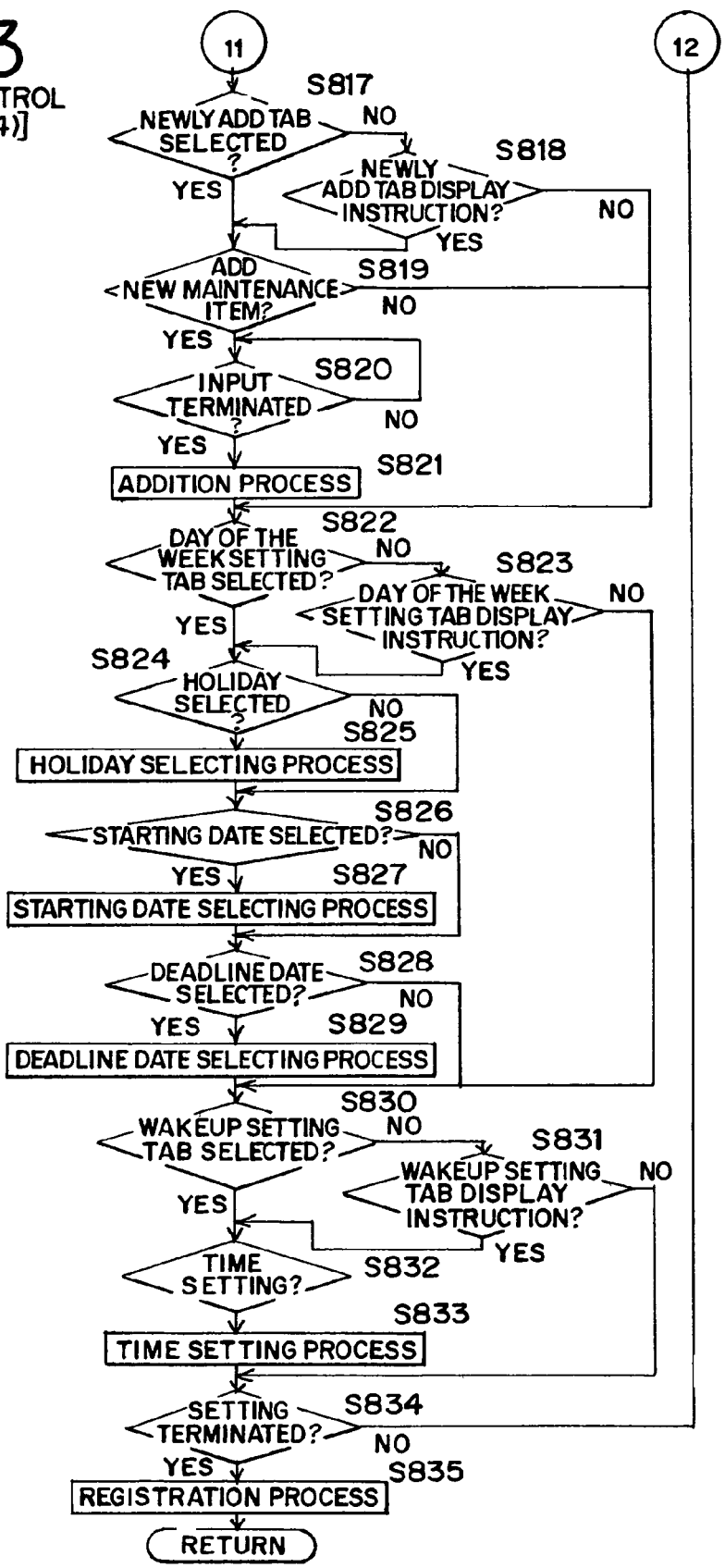
FIG. 13 is a sub-routine for describing a process for setting a display condition of a calendar display executed in step S8 of the flowchart shown in FIG. 5.

The process of setting the display condition of the calendar display executed in step S8 will now be described. FIGS. 12 and 13 are sub-routines for describing the process of setting the display condition of the calendar display executed in step S8 of the flowchart shown in FIG. 5. FIGS. 14 to 17 are views showing a dialogue window for setting the display condition. First, FIGS. 14 to 17 will be described, and thereafter, the process flow for setting the display condition of the calendar display will be described.

If "customize" is selected form the "screen operation" submenu displayed on the menu bar of the menu bar B1 (Yes in step S7) when the schedule menu screen W3 is displayed on the display unit 4b, A customize dialogue D2 (FIG. 14) enabling customization of the display condition etc. of the calendar is displayed overlapping the front surface of the schedule menu screen W3 (step S801).

As shown in FIGS. 14 to 17, the customize dialogue D2 is arranged with tab selecting region D20 for selecting a tab to set a cycle of maintenance item, new maintenance item, holiday setting, and a wakeup time of the apparatus, and "OK" button D21 for recording the set calendar display condition in the hard disc 401d of the control unit 4a and closing the dialogue.

The tab selecting region D20 includes a maintenance cycle setting tab "every day", a maintenance cycle setting tab "every week", and a maintenance cycle setting tab "every month" for setting the selected maintenance item as maintenance items to be performed every day, every week, and every month, respectively; a maintenance item "newly add" tab for newly setting the maintenance item; a "day of the week setting" tab for changing the holiday of the calendar according the usage environment of the apparatus; and a "wakeup setting" tab for setting the wakeup time of the measuring device 2. The "OK" button D21 is displayed commonly to all the tabs.

Figure 14:
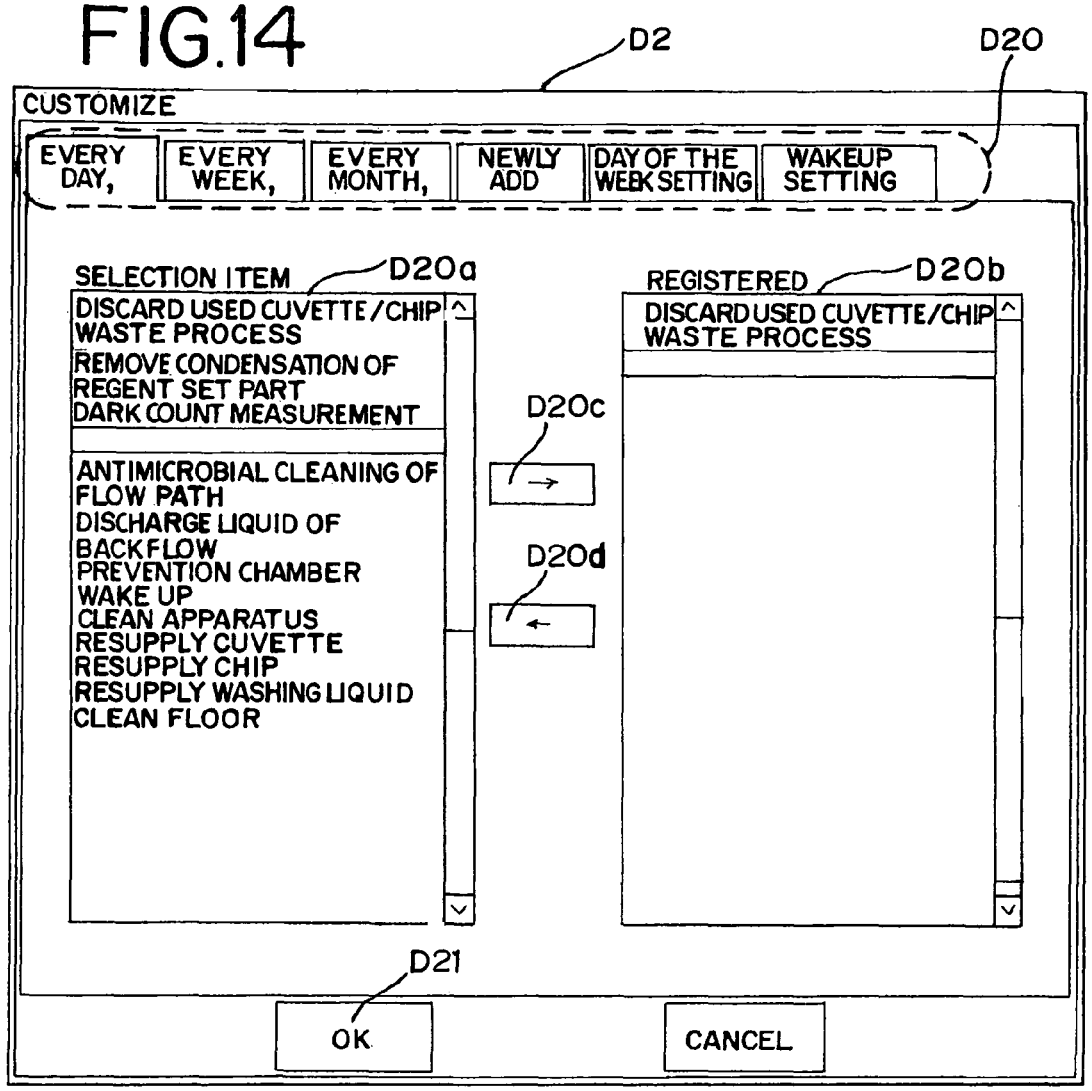
FIG. 14 is a view showing a dialogue window for setting the display condition of the calendar shown in FIGS. 9 and 10.

The maintenance cycle setting tab (every day), the maintenance cycle setting tab (every week), and the maintenance cycle setting tab (every month) allow setting of the cycle of the cyclic maintenance item displayed on the calendar. As shown in FIG. 14, the maintenance cycle setting tab (every day) includes a selection item list D20a for showing a list of options of the maintenance items that can be displayed on the calendar and a registration item list D20b or a field for setting the maintenance items to be performed every day.

In the maintenance cycle setting tab (every day), an insertion button D20c for inserting the maintenance item selected by a cursor of the selection item list D20a to a cursor position of the registration item list D20b, and a cancel button D20d for returning the maintenance item inserted to the registration item list D20b back to the selection item list D20a are arranged.

When the user pushes the button D20c, D20d, the maintenance item desired to be performed every day can be moved from the selection item list D20a to the registration item list D20b, and the maintenance item desired to be performed every day can be freely selected by the user. When the "OK" button D21 is pushed and the setting of the selected maintenance item is confirmed, the set display item is stored in the hard disc 401d of the control unit 4a, and the set conditions (maintenance schedule) is displayed on the calendar displayed in the calendar display region B5. The maintenance cycle setting tab (every week) and the maintenance cycle setting tab (every month) differ only in that the setting of the cycle is either every week or every month, and thus the description thereof will be omitted here.

Figure 15:
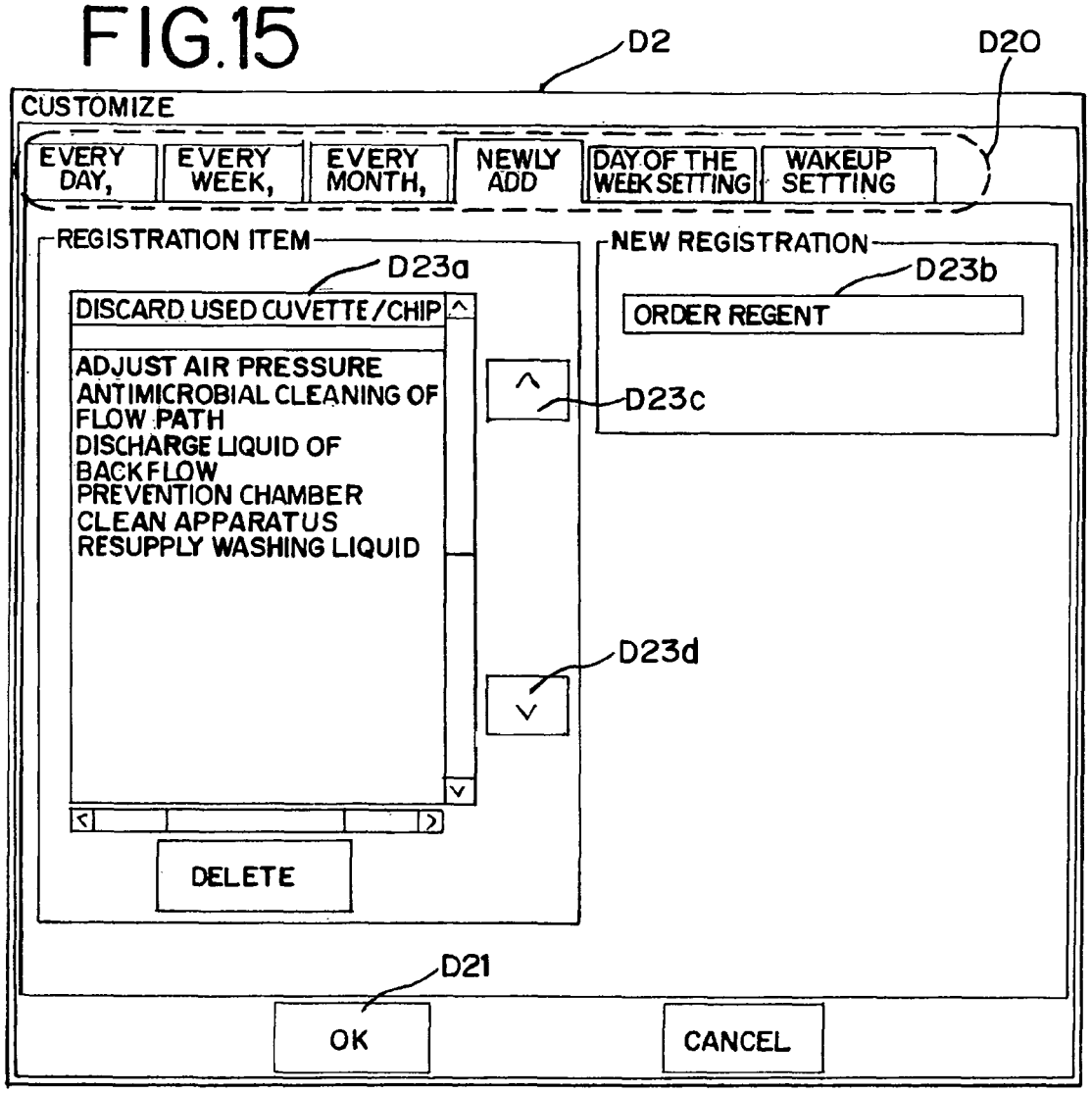
FIG. 15 is a view showing a dialogue window for setting the display condition of the calendar shown in FIGS. 9 and 10.

In the maintenance item newly add tab of FIG. 15, the setting (new, delete, edit) of the maintenance items other than those set at default are executed. The maintenance item newly add tab is arranged with a maintenance item list unit D23a for displaying a list of maintenance items registered in the hard disc 401d of the control unit 4a, a maintenance item name display unit D23b for displaying the name of the maintenance item selected with a cursor in the maintenance item list unit D23a, a "move up" button D23c for moving the cursor for selecting the maintenance item up by one in the maintenance item list unit D23a, and a "move down" button D23d for moving the cursor for selecting the maintenance item downward by one in the maintenance item list unit D23a.

When adding a new maintenance item, the user first uses the move up button D23c and the move down button D23d to move the cursor for selecting the maintenance item to a blank space in the maintenance item list unit D23a. The user then inputs the name of a new maintenance item to the maintenance item name display unit D23b. When desirably setting (changing) the name of the maintenance item, the user positions the cursor on the maintenance item to change the name, and inputs the name in the maintenance item name display unit D23b. As shown in FIG. 15, the user may use the keyboard 4c to change the maintenance item set in the maintenance item name display unit D23b to the name "order reagent". The name can be changed only for the newly added item, and the name cannot be changed for the default set maintenance item. The maintenance item of default set in advance and the maintenance item added by the user are displayed in the maintenance item list unit D23a. For easy identification, the default maintenance item is displayed in blue and the added maintenance item is displayed in red.

Figure 16:
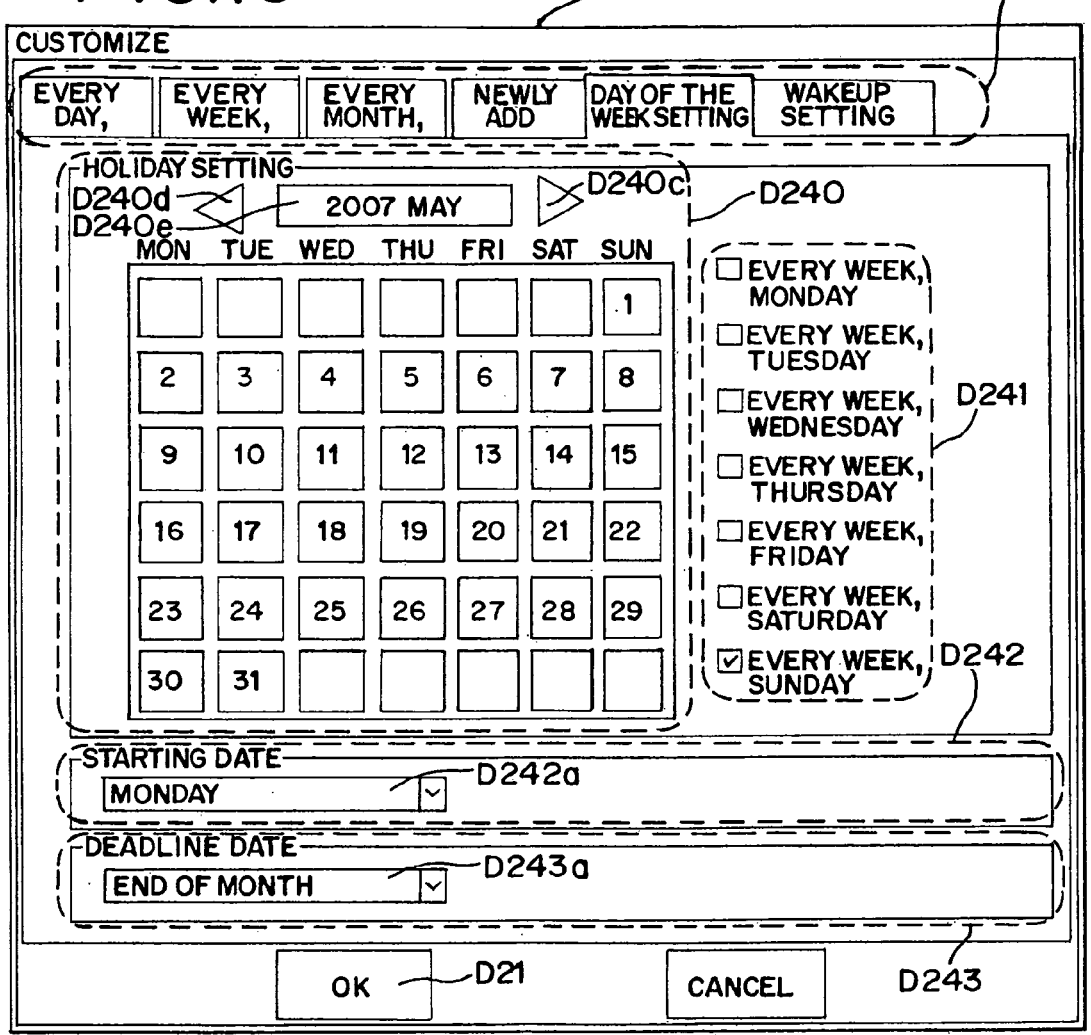
FIG. 16 is a view showing a dialogue window for setting the display condition of the calendar shown in FIGS. 9 and 10.

As shown in FIG. 16, the day of the week setting tab includes a setting auxiliary calendar display region D240 for displaying the calendar set with holidays, a holiday setting checkbox display region D241 displaying a check box for performing holiday setting of the calendar displayed in the setting auxiliary calendar display region D240 and the calendar display region B5, a "starting date" setting region D242 for setting the day of the week for starting the week of the calendar displayed on the setting auxiliary calendar display region D240, and a "deadline date" setting region D243 used in examination result report, accounting report, and the like for every month.

The setting auxiliary calendar display region D240 includes a calendar year/month display part D240a for displaying "year and month" of the calendar for setting the holiday, a calendar display part D240b for displaying the calendar displayed in the calendar year/month display part, a "next month" button D240c for changing the calendar displayed on the calendar display part B510b to one month ahead, and a "previous month" button D240d for changing the calendar displayed on the calendar display part to one month before.

In the holiday setting check box display region D241, the check box group for setting every Monday to every Sunday as holidays is arranged. When the checkboxes are checked, the checked day of the week is set as the holiday, the holiday is displayed in red in the calendar displayed on the setting auxiliary calendar display region D240, and the setting is reflected on the calendar displayed on the calendar display region B5. In the present embodiment, an example of setting Sunday as the holiday is shown. By this, weekdays may be set as holidays according to the usage state of the apparatus of each facility.

The "starting date" setting region D242 includes a starting date selection combo box D242a for selecting the day of the week that comes to the head of the week of the calendar displayed on the calendar display part B510b. When the starting date selection combo box D242a is clicked by an input means such as a mouse, a selection menu (not shown) from Monday to Sunday is displayed, and an arbitrary day of het week is selected.

The "deadline date" setting region D243 includes a deadline date setting combo box D243a for setting the beginning of the month and the end of the month of the calendar displayed on the calendar display part B510b as deadline date. When the deadline date setting combo box D243a is clicked by the input means such as a mouse, a selection menu (not shown) such as beginning of the month and the end of the month is displayed, and the beginning of the month or the end of the month can be arbitrarily set as the deadline date. The beginning of the month is the first date excluding the holiday displayed on the calendar display part B510b, and the end of the month is the last date excluding the holiday displayed on the calendar display part B510b. Thus, the deadline date of examination result report, accounting report, and the like for every month can be displayed on the calendar, whereby the convenience of the apparatus can be further enhanced.

Figure 17:
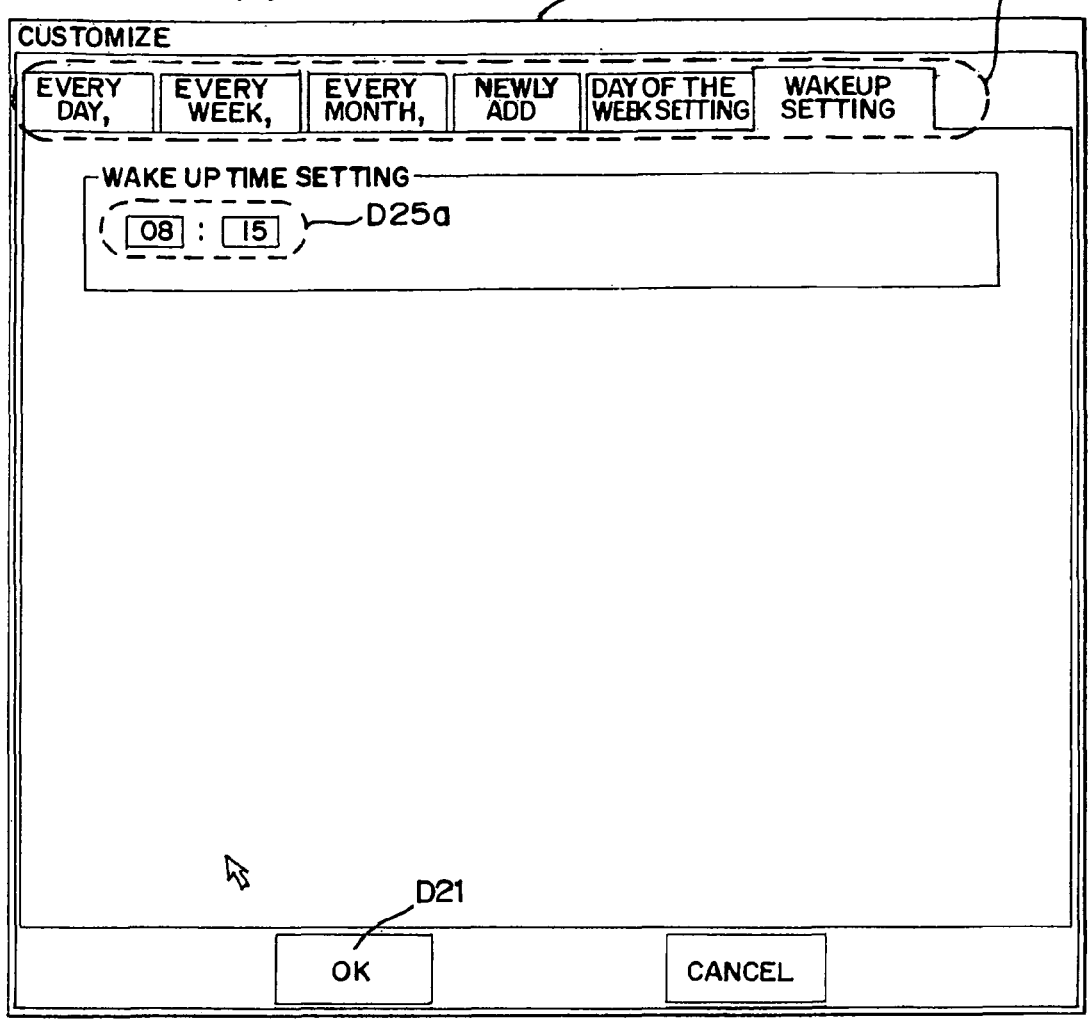
FIG. 17 is a view showing a dialogue window for setting the display condition of the calendar shown in FIGS. 9 and 10.

As shown in FIG. 17, the wakeup setting tab includes a reference wakeup time setting part D25a for setting the wakeup time that serves as a reference. When the user inputs the time to the reference wakeup time setting part D25a using the keyboard 5c etc., the power of the immune analyzer 1 is automatically turned ON so that a standby state in which measurement can be performed is obtained at the input time, and the control unit 2a performs the wakeup operation for temperature adjusting the detector 15, the reagent installing unit 6 and the reagent installing unit 7. The input time is set as the reference wakeup time. The wakeup operation can be set with the performing cycle similar to the maintenance item. In the present embodiment, as shown in FIG. 14, the wakeup operation is handled as one item which performing cycle can be changed, and a cycle of once a month, once a week, or every day can be set. In FIG. 9, a case where the cycle of the wakeup operation is set to every day, and the reference wakeup time is 8:15 is shown.

The wakeup time can be set individually besides the standard wakeup time. In this case, the user individually clicks the wakeup icon B510e of the date on which the wakeup time is desirably set, displays the wakeup time change dialogue on the display unit 4b, and inputs the desired wakeup time using the keyboard 4c. Thus, the reference wakeup time can be changed for every date.

The flow shown in FIGS. 12 and 13 will be described using FIGS. 14 to 17 described above.

If "customize" is selected from the "operation screen" submenu displayed on the menu bar of the menu bar B1 when the schedule menu screen W3 is displayed on the display unit 4b (Yes in step S7 of FIG. 5), the customize dialogue D2 in which customization of the display condition etc. of the calendar is performed is displayed overlapping the front surface of the schedule menu screen W3 (step S801).

Whether or not the maintenance cycle setting tab (every day) is selected is determined in step S802. If the maintenance cycle setting tab (every day) is selected (Yes in step S802), whether or not the maintenance item scheduled to be performed every day is selected with the cursor is determined in step S804. If the maintenance item scheduled to be performed every day is selected (Yes in step S804), whether or not to add the maintenance item scheduled to be performed every day from the selection item list D20a to the registration item list D20b in step S805. When adding the maintenance item scheduled to be performed every day from the selection item list D20a to the registration item list D20b (Yes in step S805), the buttons D20c, D20d are pushed to perform the process of adding the maintenance item scheduled to be performed every day in step S806.

If the maintenance cycle setting tab (every day) is not selected (No in step S802), whether or not the display instruction of the maintenance cycle setting tab (every day) is made is determined in step S803. If the display instruction of the maintenance cycle setting tab (every day) is made (Yes in step S803), the process proceeds to step S804. If the determination is No in steps S803, 804, and 805, the process proceeds to step S807.

In step S807, the CPU 401a determines whether the maintenance cycle setting tab (every week) is selected. If the maintenance cycle setting tab (every week) is selected (Yes in step S807), whether or not the maintenance item scheduled to be performed every week is selected with the cursor is determined in step S809. If the maintenance item scheduled to be performed every week is selected with the cursor (Yes in step S809), whether or not to add the maintenance item scheduled to be performed every week is determined in step S810. If the maintenance item scheduled to be performed every week is to be added (Yes in step S810), the buttons D20c, D20d are pushed to perform the process of adding the maintenance item scheduled to be performed every week in step S811.

If the maintenance cycle setting tab (every week) is not selected (No in step S807), whether or not the display instruction of the maintenance cycle setting tab (every week) is made is determined in step S808. If the display instruction of the maintenance cycle setting tab (every week) is made (Yes in step S808), the process proceeds to step S809. If the determination is No in steps S808, 809, and 810, the process proceeds to step S812.

In step S812, the CPU 401a determines whether the maintenance cycle setting tab (every month) is selected. If the maintenance cycle setting tab (every month) is selected (Yes in step S812), whether or not the maintenance item scheduled to be performed every month is selected with the cursor is determined in step S814. If the maintenance item scheduled to be performed every month is selected with the cursor (Yes in step S814), whether or not to add the maintenance item scheduled to be performed every month is determined in step S815. If the maintenance item scheduled to be performed every month is to be added (Yes in step S815), the buttons D20c, D20d are pushed to perform the process of adding the maintenance item scheduled to be performed every month in step S816.

If the maintenance cycle setting tab (every month) is not selected (No in step S812), whether or not the display instruction of the maintenance cycle setting tab (every month) is made is determined in step S813. If the display instruction of the maintenance cycle setting tab (every month) is made (Yes in step S813), the process proceeds to step S814. If the determination is No in steps S813, 814, and 815, the process proceeds to step S817.

In step S817, the CPU 401a determines whether or not the maintenance item newly add tab is selected. If the maintenance item newly add tab is selected (Yes in step S817), (see FIG. 15) is selected, and whether or not the new addition of the maintenance is executed is determined in step S819. If selected (Yes in step S819), whether or not the name of the new maintenance item is input to the maintenance item name display unit D23b is determined in step S820. If the name of the new maintenance item is input to the maintenance item name display unit D23b, the new maintenance item is added to the maintenance item list unit D23a (step S821).

If the maintenance item newly add tab is not selected (No in step S817), whether or not the display instruction of the maintenance item newly add tab is made is determined in step S818. If the display instruction of the maintenance item newly add tab is made (Yes in step S818), the process proceeds to step S819. The process proceeds to step S822 if the determination in steps S818, 819 is No.

In step s822, the CPU 401a determines whether or not the day of the week setting tab is selected. If the day of the week setting tab is selected (Yes in step S822), whether or not the checkbox of each day of the week arranged in the holiday setting check box display region D241 is changed is determined in step S824. If the check box is changed (Yes in step S823), the check result is reflected on the calendar displayed on the setting auxiliary calendar display region D240, and the checked day of the week is displayed in red (step S825). In step S826, the CPU 401a determines whether or not the starting date selection combo box 242a is clicked. If the combo box D242a is clicked (Yes in step S826), a certain day of the week is selected as the day of the week that comes at the head of the week of the calendar displayed on the calendar display part B510b (step S827). In step S828, the CPU 401 determines whether or not the deadline date setting combo box D243a is clicked. If the deadline date setting combo box D243a is clicked (Yes in step S828), the beginning of the month or the end of the month are arbitrarily set as the deadline date (step S829).

If the day of the week setting tab is not selected (No in step S822), whether or not the display instruction of the day of the week setting tab is made is determined in step S823. If the display instruction of the day of the week setting tab is made (Yes in step S823), the process proceeds to step S824. The process proceeds to step S826 if the determination is No in step S824, the process proceeds to step S828 if the determination is No in step S826, and the process proceeds to step S830 if the determination is No in steps S823 and S828.

In step S830, the CPU 401a determines whether or not the wakeup setting tab is selected. If the wakeup setting tab is selected (Yes in step S830), the time at which the apparatus becomes the standby state in which measurement can be performed is input to the reference wakeup time setting part D25a by the user in step S832. If the wakeup setting tab is not selected (No in step S830), whether or not the display instruction of the wakeup setting tab is made is determined in step S831. If the display instruction of the wakeup setting tab is made (Yes in step S831), the process proceeds to step S832. In step S832, whether or not the time is input to the reference wakeup time setting part D25a is determined (step S833). If No in the determination of step S831, the process proceeds to step S834.

The CPU 401a determines whether or not the OK button D21 indicating the termination of the setting is pushed. If the OK button D21 is pushed (Yes in step S834), the set display condition of the calendar is recorded in the hard disc 401d of the control unit 4a, the dialogue is closed, and the process of step S8 is terminated. If the OK button D21 is not pushed (No in step S834), the process again returns to S802.

[Change of Wakeup Time]

Figure 18:
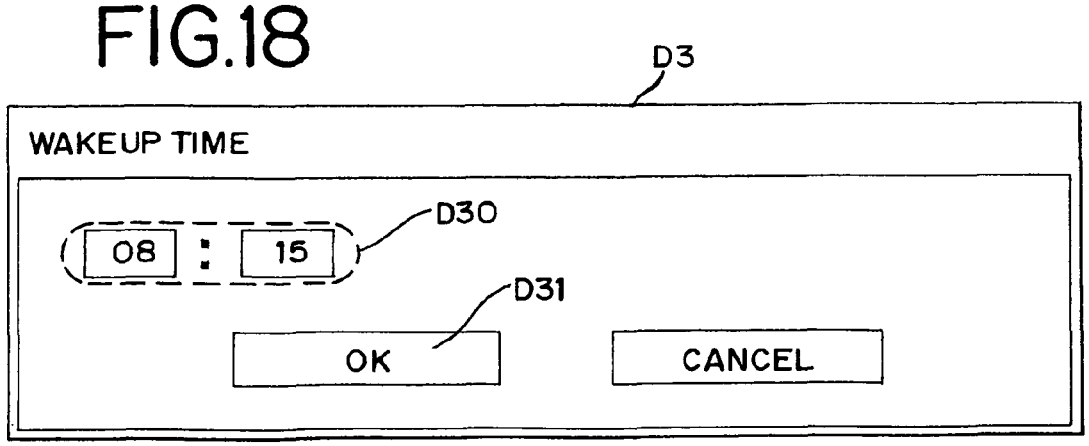
FIG. 18 is a view showing a dialogue window for changing the wakeup time set by the wakeup setting tab shown in FIG. 17.

A case of changing the set reference wakeup time for every date with the wakeup setting tab will now be described in detail. When the wakeup icon B501e (see FIG. 9) is clicked, the wakeup time change dialogue D3 shown in FIG. 18 is displayed.

The wakeup time change dialogue D3 includes a change wakeup time setting part D30 for inputting the wakeup time to be changed, and an "OK" button D31 for recording the changed wakeup time to the hard disc 401d of the control unit 4a and closing the dialogue. The reference wakeup time is displayed on the change wakeup time setting part D30 displayed on the wakeup time change dialogue D3 after the wakeup icon B501e is clicked.

When desirably changing the reference wakeup time, the user uses the keyboard 5c etc. to input the desired wakeup time to the change wakeup time setting part D30. After the input, the user pushes the "OK" button D31 to change the standard wakeup time of a specified date to the wakeup time desired by the user.

The embodiment disclosed herein is merely illustrative in all aspects and should not be recognized as being exclusive. The scope of the invention is defined by the scope of the claims rather than by the description of the embodiment, and meaning equivalent to the claims and all modifications within the scope is encompassed herein.

In the present embodiment, a configuration in which the customize dialogue D2 includes a maintenance cycle setting tab "every day", a maintenance cycle setting tab "every week", and a maintenance cycle setting tab "every month" for setting the selected maintenance item as maintenance items to be performed every day, every week, and every month, respectively; a maintenance item "newly add" tab for newly setting the maintenance item; a "day of the week setting" tab for changing the holiday of the calendar according the usage environment of the apparatus; and a "wakeup setting" tab for making measuring device 2 in a standby state at which the measurement can immediately be performed arranged in the tab selecting region D20 is described, but is not limited thereto, and a dialogue with the cycle setting tabs and a dialogue with other setting tabs may be separated in order to realize a user interface in which change frequency of the user is more easier to understand.

The invention claimed is:

1. A sample analyzing apparatus comprising:
a measuring unit for measuring a specimen;
a memory for storing a schedule of maintenance of the measuring unit;
a display;
a controller for displaying on the display a screen of calendar format, wherein the screen includes date display areas for displaying dates for a month and maintenance item display areas, each of the maintenance item display areas is arranged corresponding to each of the date display areas and displays a maintenance item scheduled on the corresponding date; and
an automatic maintenance item acceptor for accepting a specification of a maintenance item involving an automatic maintenance operation;
wherein the controller causes the measuring unit to execute the automatic maintenance operation of the specified maintenance item when the automatic maintenance item acceptor accepts the specification of the maintenance item, and updates the screen of calendar format so that the executed maintenance item is not displayed on the maintenance item display area and the corresponded date of the executed maintenance item is displayed on the date display area.

2. The sample analyzing apparatus of claim 1, further comprising an acceptor for accepting a specification of a date from a user; wherein the controller displays on the display a window for displaying a maintenance item scheduled to be performed on the date when the acceptor accepts the specification.

3. The sample analyzing apparatus of claim 1, further comprising a performed item acceptor for accepting a specification of a maintenance item performed by a user; wherein the controller stores the performed maintenance item in the memory when the performed item acceptor accepts the specification of the performed maintenance item.

4. The sample analyzing apparatus of claim 3, wherein the controller displays on the display the screen of calendar form in which the performed maintenance item is not displayed when the performed item acceptor accepts the specification of the performed maintenance item.

5. The sample analyzing apparatus of claim 2, wherein the controller displays the window which displays a performed maintenance item and a non-performed maintenance item when the acceptor accepts the specification.

6. The sample analyzing apparatus of claim 1, further comprising a maintenance period setter for setting a period of performing a periodic maintenance item; wherein the controller displays the maintenance item on the display screen of calendar format in a period set by the maintenance period setter.

7. The sample analyzing apparatus of claim 6, wherein the period is one of daily, weekly, or monthly.

8. The sample analyzing apparatus of claim 7, further comprising:
a holiday setter for setting a holiday; wherein the controller displays a maintenance item scheduled to be performed daily on dates other than the holidays set by the holiday setter in the screen when the period set by the maintenance item period setter is daily.

9. The sample analyzing apparatus of claim 1, wherein the controller stores the maintenance item executed with automatic maintenance in the memory.

10. The sample analyzing apparatus of claim 1, further comprising a maintenance item setter for a user to set a new maintenance item, wherein the controller stores the maintenance item set by the maintenance item setter in the memory.

11. The sample analyzing apparatus of claim 1, further comprising a standby time setter for setting a time at which a standby state during which the measuring unit is able to start the measurement of the specimen is obtained, wherein the controller activates the measuring unit based on the standby time so that the measuring unit is in the standby state at the standby time set by the standby time setter.

12. The sample analyzing apparatus of claim 11, wherein the controller displays on the screen of calendar format a date, a maintenance item scheduled to be performed on the date, and a standby time display icon for calling out a display of the standby time set by the standby time setter in correspondence to each other, and displays the standby time on the display when the standby time display icon is operated.

13. The sample analyzing apparatus of claim 12, wherein the controller displays a window for displaying the standby time when the standby time display icon is operated, the window being able to accept the standby time.

14. A sample analyzing apparatus comprising:
a measuring unit for measuring a specimen;
a memory for storing a maintenance item of the measuring unit and a scheduled date for performing the maintenance item in correspondence to each other as a schedule of maintenance;
a display;
a controller for displaying on the display a screen including date display area for displaying a date and a maintenance item display area for displaying a maintenance item scheduled on the date; and
an automatic maintenance item acceptor for accepting a specification of a maintenance item involving an automatic maintenance operation;
wherein the controller causes the measuring unit to execute the automatic maintenance operation of the specified maintenance item when the automatic maintenance item acceptor accepts the specification of the maintenance item, and updates the displayed screen so that the executed maintenance item is not displayed on the maintenance item display area and the corresponded date of the executed maintenance item is displayed on the date display area.

15. A method for displaying maintenance schedule of a measuring unit for measuring a specimen provided in a sample analyzing apparatus, comprising steps of:
providing a screen of calendar format, which includes date display areas for displaying dates for a month and maintenance item display areas, each of the maintenance item display areas is arranged corresponding to each of the date display areas and displays a maintenance item scheduled on the date;
displaying the screen on a display of the sample analyzing apparatus;
accepting a specification of a maintenance item involving an automatic maintenance operation;
executing the automatic maintenance operation of the specified maintenance item when the automatic maintenance item acceptor accepts the specification of the maintenance item, and
updating the screen of calendar format so that the executed maintenance item is not displayed on the maintenance item display area and the corresponded date of the executed maintenance item is displayed on the date display area.

16. The method of claim 15, further comprising a step of accepting a specification of a date from a user, and a step of displaying a window for displaying a maintenance item scheduled to be performed on the date when the acceptor accepts the specification.

17. The method of claim 15, further comprising a step of accepting a specification of a maintenance item performed by a user, and a step of storing the performed maintenance item in a memory.

* * * * *